US008088381B2

(12) United States Patent
Langsetmo Parobok et al.

(10) Patent No.: US 8,088,381 B2
(45) Date of Patent: Jan. 3, 2012

(54) METHODS OF TREATMENT OF CARDIOVASCULAR DISEASE USING ANTI-CTGF AGENTS

(75) Inventors: Ingrid Langsetmo Parobok, Montara, CA (US); Christopher T. Jacob, Santa Clara, CA (US); David Y. Liu, Palo Alto, CA (US)

(73) Assignee: FibroGen, Inc., San Francisco, CA (US)

( * ) Notice: Subject to any disclaimer, the term of this patent is extended or adjusted under 35 U.S.C. 154(b) by 892 days.

(21) Appl. No.: 11/418,624

(22) Filed: May 5, 2006

(65) Prior Publication Data

US 2006/0281667 A1 Dec. 14, 2006

Related U.S. Application Data

(60) Provisional application No. 60/734,433, filed on Nov. 7, 2005, provisional application No. 60/690,957, filed on Jun. 15, 2005, provisional application No. 60/678,495, filed on May 5, 2005.

(51) Int. Cl.
*A61K 39/395* (2006.01)
*G01N 33/49* (2006.01)

(52) U.S. Cl. .................. 424/139.1; 424/158.1; 424/9.3; 436/501; 702/19; 702/45; 702/46; 702/50

(58) Field of Classification Search ........................ None
See application file for complete search history.

(56) References Cited

U.S. PATENT DOCUMENTS

| | | | |
|---|---|---|---|
| 5,408,040 A | 4/1995 | Grotendorst et al. | |
| 5,783,187 A | 7/1998 | Grotendorst et al. | |
| 7,384,634 B2 * | 6/2008 | Grotendorst et al. | 424/145.1 |
| 7,405,274 B2 * | 7/2008 | Lin et al. | 530/387.1 |
| 7,541,438 B2 * | 6/2009 | Tamatani et al. | 530/387.1 |
| 7,871,617 B2 * | 1/2011 | Lin et al. | 424/139.1 |
| 2003/0166011 A1 | 9/2003 | Tamatani et al. | |
| 2004/0092450 A1 | 5/2004 | Grotendorst et al. | |
| 2004/0248206 A1 | 12/2004 | Lin et al. | |
| 2005/0059629 A1 * | 3/2005 | Gaarde et al. | 514/44 |

FOREIGN PATENT DOCUMENTS

| | | |
|---|---|---|
| WO | WO-96/38172 A1 | 12/1996 |
| WO | WO-99/13910 A1 | 3/1999 |
| WO | WO-99/33878 A1 | 7/1999 |
| WO | WO-00/02450 A1 | 1/2000 |
| WO | WO-00/35936 A1 | 6/2000 |
| WO | WO-00/35939 A2 | 6/2000 |
| WO | WO01/66140 * | 9/2001 |
| WO | WO-03/049773 A1 | 6/2003 |
| WO | WO-03/053340 A2 | 7/2003 |
| WO | WO-2004/108764 A2 | 12/2004 |
| WO | WO 2005/077413 A1 | 8/2005 |

OTHER PUBLICATIONS

K. Hishikawa et al., JBC 276:16797-16803, 20001.*
Opalinska et al (Nature Reviews Drug Discovery, 2002, vol. 1, pp. 503-514).*
Scanlon (Curr. Pharm. Biotech. 5:415-420, 2004).*
Grossman et al (Neuro-Oncology 6: 32-40, 2004).*
Moulder et al (Clin. Cancer Res. 14(23): 7909-7916, 2008).*
Rudin et al (J. Clin. Oncol.26(6): 870-876, 2008).*
Agrawal et al (Mol. Med. Today 6:72-81, 2000).*
Oemar et al., 1997, Circulation 95(4):831-839.*
Ahmed, Mohammed Shakil, et al., "Connective Tissue Growth Factor—A Novel Mediator of Angiotensin II-Stimulated Cardiac Fibroblast Activation in Heart Failure in Rats," J. Mol. Cell. Cardiol., vol. 36, 2004, pp. 393-404.
Candido, Riccardo, et al., "A Breaker of Advanced Glycation End Products Attenuates Diabetes-Induced Myocardial Structural Changes," Circulation Res., vol. 92, 2003, pp. 785-792.
Duncan, Matthew R., et al., "Connective Tissue Growth Factor Mediates Transforming Growth Factor B-Induced Collagen Synthesis: Down-Regulation by cAMP," FASEB J., vol. 13, Oct. 1999, pp. 1774-1786.
Ertl, R.F., et al., "Prostaglandin E Inhibits Fibroblast Recruitment," Am. Rev. Respir. Dis., vol. 145, No. 4, Apr. 1992, pp. A19.
Finkenberg, Piet, et al., "Angiotensin II Induces Connective Tissue Growth Factor Gene Expression Via Calcineurin-Dependent Pathways," Am. J Pathol., vol. 163, No. 1, Jul. 2003, pp. 355-366.
Jaffa, Ayad, et al., "Elevated CTGF Levels Are an Independent Risk Marker of Diabetic Vascular Disease," American Society of Nephrology Annual Meetin Abstract, J. Am. Society of Nephrology, vol. 16, Oct. 2005, pp. 636A.
Kapoun, Ann M., et al., "B-Type Natriuretic Peptide Exerts Broad Functional Opposition to Transforming Growth Factor-B in Primary Human Cardiac Fibroblasts," Circulation Res., vol. 94, 2004, pp. 453-461.
Kohyama, Tadashi, et al., "PDE4 Inhibitors Attenuate Fibroblast Chemotaxis and Contraction of Native Collagen Cells," Am. J. Resp. Cell. Mol. Biol., vol. 26, 2002, pp. 694-701.
Kondo, Seiji, et al., "Characterization of a Mouse ctgf-3' -UTR Segment That Mediates Repressive Regulation of Gene Expression," Biochem Biophys. Res. Comm., vol. 278, 2000, pp. 119-124.
Kothapalli, Devashish, et al., "Transforming Growth Factor B Induces Anchorage-Independent Growth of NRK Fibroblasts Via a Connective Tissue Growth Factor-Dependent Signaling Pathway," Cell Growth Differ., vol. 8, Jan. 1997, pp. 61-68.
Lawson, Sibi R., et al., "Enhanced Dermal and Retinal Vascular Permeability in Streptozotocin-Induced Type 1 Diabetes in Wistar Rats: Blockade With a Selective Bradykinin B1 Receptor Antagonist," Reg. Peptides, vol. 124, 2005, pp. 221-224.
Matsuoka, Hiroto, et al., "A p38 MAPK Inhibitor, FR-167653, Ameliorates Murine Bleomycin-Induced Pulmonary Fibrosis," Am. J. Physiol. Lung Cell. Mol. Physiol., vol. 283, 2002, pp. L103-L112.
Peng, Hongmei, et al., "Ac-SDKP Reverses Cardiac Fibrosis in Rats With Renovascular Hypertension," Hypertension, vol. 42, 2003, pp. 1164-1170.
Ricupero, Dennis A., et al., "Regulation of Connective Tissue Growth Factor by Prostaglandin E2," Am. J. Physiol., vol. 277, 1999, pp. L1165-L1171.

(Continued)

*Primary Examiner* — Lorraine Spector
(74) *Attorney, Agent, or Firm* — Leanne C. Price, Esq.; Paul E. Borchardt

(57) ABSTRACT

The present invention relates to methods for treating impaired cardiac function. Methods for treating various physiological and pathological features associated with cardiac dysfunction by administering an agent that inhibits the expression or activity of connective tissue growth factor (CTGF) are provided.

9 Claims, 20 Drawing Sheets

OTHER PUBLICATIONS

Ricupero, Dennis A., et al., Des-Arg10-Kalladin Expression of the B1 Receptor Stimulates Type 1 Collagen Synthesis Via Stabilization of Connective Tissue Growth Factor mRNA, J. Biol. Chem., vol. 275, No. 17, Apr. 2000, pp. 12475-12480.

Ruperez, Monica, et al., "Connective Tissue Growth Factor is a Mediator of Angiotensin II-Induced Fibrosis," Circulation, vol. 108, 2003, pp. 1499-1505.

Shimo, Tsuyoshi, et al., "Inhibition of Endogenous Expression of Connective Tissue Growth Factor by Its Antisense Oligonucleotide and Antisense RNA Supresses Proliferation and Migration of Vascular Endothelial Cells," J. Biochem., vol. 124. 1998. pp. 130-140.

Tan, Yan, et al., "Mechanisms Through Which Bradykinin Promotes Glomerular Injury in Diabetes," Am. J. Physiol. Renal Physiol., vol. 288, 2005, pp. F483-F492.

Uchio, Kozue, et al., "Down-Regulation of Connective Tissue Growth Factor Type 1 Collagen mRNA Expression by Connective Tissue Growth Factor Antisense Oligonucleotide During Experimental Liver Fibrosis," Wound Repair Regen., vol. 12, No. 1, 2004, pp. 60-66.

Way, Kerrie J., et al., "Expression of Connective Tissue Growth Factor is Increased in Injured Myocardium Associated With Protein Kinase C B2 Activation and Diabetes," Diabetes, vol. 51, Sep. 2002, pp. 2709-2718.

Wilkinson-Berka, Jennifer L., et al., "Angiotensin and Bradykinin: Targets for the Treatment of Vascular and Neuro-Glial Pathology in Diabetic Retinopathy," Current Pharma. Design, vol. 10, 2004, pp. 3313-3330.

Yosimichi, Gen, et al., "CTGF/Hcs24 Induces Chondrocyte Differentiation Through a p38 Mitogen-Activated Protein Kinase (p38MAPK) and Proliferation Through a p44/42 MAPK/Extracellular-Signal Regulated Kinase (ERK)," Eur. J. Biochem., vol. 268, 2001, pp. 6058-6065.

* cited by examiner

METHODS OF TREATMENT OF CARDIOVASCULAR DISEASE USING ANTI-CTGF AGENTS

This application claims the benefit of U.S. Provisional Application Ser. No. 60/678,495, filed on 5 May 2005, U.S. Provisional Application Ser. No. 60/690,957, filed on 15 Jun. 2005, and U.S. Provisional Application Ser. No. 60/734,433, filed on 7 Nov. 2005, each of which is incorporated by reference herein it its entirety.

FIELD OF THE INVENTION

The present invention relates to methods and agents for treating impaired vascular and cardiac function. Methods and agents for treating various physiological and pathological features associated with vascular dysfunction and cardiac dysfunction are also provided.

BACKGROUND OF THE INVENTION

Vascular complications of diabetes are devastating, and can affect every major organ. Patients with diabetes have an increased incidence of atherosclerosis, and of cardiovascular, peripheral vascular, and cerebrovascular disease. Vascular complications and disease account for most of the mortality and morbidity of diabetic individuals.

Numerous factors contribute to the development of vascular disease in patients with diabetes, including hyperglycemia, hypertension, obesity, and dyslipidemia. For example, elevated blood glucose levels (i.e., hyperglycemia) are believed to be a primary cause of microvascular complications, including retinopathy, nephropathy, and neuropathy, and to play a role in the premature and accelerated development of macrovascular complications, such as cardiovascular disease and peripheral vascular disease. Elevated blood glucose levels and oxidant stress, both characteristic of the diabetic microenvironment, accelerate advanced glycation end-product (AGE) formation. Hyperglycemia and AGEs can cause changes (e.g., damage) to the normal structure and function of the endothelium and can lead to endothelial dysfunction. In addition, hyperglycemia and AGEs have been associated with various vascular complications, including damage to the body's microvasculature and macrovasculature. Further, hyperglycemia and dyslipidemia are associated with intima-media thickness, a recognized marker for cardiovascular and cerebrovascular disease.

Cardiovascular complications of diabetes mellitus are severe and significantly contribute to the morbidity and mortality rates of the disease. These complications include coronary heart disease (CHD), congestive heart failure, stroke, peripheral arterial disease, cardiomyopathy, nephropathy, retinopathy, and neuropathy.

Vascular disease can occur in diabetic patients in association with other complications, such as, for example, diabetic nephropathy, a common and often severe condition. Cardiovascular disease is the leading cause of death among diabetic patients with end-stage renal disease (ESRD). (McMillan et al. (1990) BMJ 301:540-544; Hirschl et al. (1992) Am J Kidney Dis. 20:564-568; and Rischen-Vos et al. (1992) Nephrol Dial Transplant 7:433-437.)

Patients with diabetes are at critical risk for congestive heart failure. A number of factors contribute to the high incidence of diabetic cardiomyopathy, including prolonged hypertension, chronic hyperglycemia, severe coronary atherosclerosis, etc. Mortality from stroke is increased almost 3-fold when patients with diabetes are matched to those without diabetes. (Stamler et al. (1993) *Diabetes Care* 16:434-444.) Further, diabetes increases the likelihood of severe carotid atherosclerosis. (Folsom et al. (1994) Stroke 16:434-444. and O'Leary et al. (1992) Stroke 25:66-73.)

The incidence of peripheral vascular disease (PVD) is about 4 times greater in patients with diabetes than patients without diabetes. (See, e.g., Gibbons (1998) Peripheral vascular disease. In H. E. Lebovitz, ed., *Therapy for diabetes mellitus* ($3^{rd}$ edition), pp. 290-302.) Peripheral vascular disease is a condition in which the arteries in the legs, and sometimes the arms, are narrowed by atherosclerosis. It contributes to lower-extremity ulceration, impaired wound healing, and decreased ability to fight infection. The reasons for this include delayed or prevented delivery of oxygen (ischemia), nutrients, and antibiotics to the infected area and impaired immune response. (See Gibbons, supra.) Other conditions associated with diabetes, such as hypertension, obesity, and dyslipidemia, further exacerbate the diabetic patient's chances of developing PVD.

Current treatment strategies directed to treatment or reduction of the progression and severity of vascular complications of diabetes, or to prevention of the development of such complications, employ various approaches, including optimized glycemic control (through modification of diet and/or insulin therapy), hypertension control (including administration of angiotensin-converting enzyme (ACE) inhibitors and angiotensin receptor blockers (ARBs) to reduce hypertension), cholesterol-lowering treatments, etc. However, such therapies are not universally successful, and often are ineffective at reversing the vascular complications and pathology (e.g., damage) associated with diabetes or improving the function of affected vessels, organs, and tissues. Further, due to such factors as the aging of the population and a believed increase in prevalence of obesity and sedentary life habits in the United States and in the global population, the prevalence of diabetes is increasing worldwide. Thus, diabetes is a major risk factor for vascular disease on a global scale. Therefore, there is a need in the art for methods for treating vascular complications of diabetes, methods for reducing the progression and severity of these vascular complications, and methods for preventing the development of such complications. Additionally, there is a need in the art for methods and agents effective at reversing the vascular complications associated with diabetes, including reversing the pathology and damage to the vasculature, and for improving the function of vessels, organs, and tissues affected by vascular complications associated with diabetes.

The present invention meets this need by showing for the first time that specific inhibition of CTGF both reduces vascular dysfunction and measurably improves vascular function in animal models of diabetic disease. In particular, the present invention demonstrates that administration of an anti-CTGF antibody effectively reduced arterial stiffness, vascular permeability, extravasation, e.g., edema, and vascular calcification, in an animal model of diabetes. The present methods and agents also effectively reversed the pathology and damage to the vasculature associated with diabetes.

The present invention further demonstrates that specific inhibition of CTGF improves cardiac function. In particular, the present invention demonstrates that administration of an anti-CTGF antibody led to measurable improvement in cardiac function as evidenced by demonstrated improvements in the following parameters: ventricular relaxation, ventricular contractility, end diastolic pressure, end diastolic volume, ejection fraction, arterial elastance, stroke volume, and cardiac output.

SUMMARY OF THE INVENTION

Figure 1:
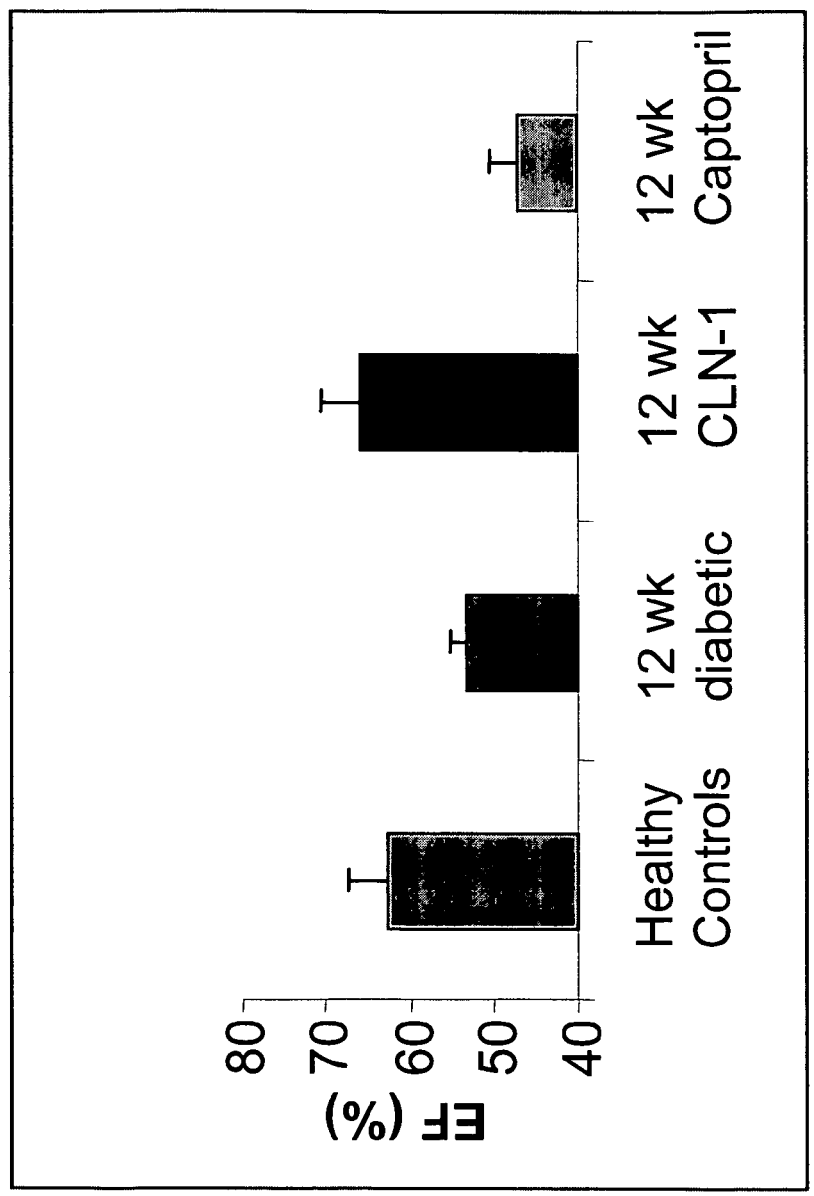
FIG. 1 shows the present methods and agents effectively improved cardiac ejection fraction in mammalian subjects.

The present invention provides a method for improving cardiac function in a subject, the method comprising administering to the subject an effective amount of an anti-CTGF agent, thereby improving cardiac function in the subject.

In various embodiments, the subject is a subject having or at risk for having diabetes.

In certain embodiments, the method may in particular be for increasing ejection fraction; increasing stroke volume; increasing cardiac output; increasing ventricular relaxation; increasing ventricular contractility; reducing end diastolic pressure; or reducing end diastolic volume.

The methods of the present invention are particularly contemplated for treating or preventing a cardiac complication. For example, the cardiac complication may be selected from cardiohypertrophy, congestive heart failure, and cardiomyopathy. In specific embodiments, the method is for treating or preventing the cardiac complication by reducing blood low density lipoprotein (LDL) levels. In certain embodiments, the cardiac complication is a cardiac complication of diabetes.

The subject of the methods may be a mammalian subject. In particular, the subject may be a human subject.

The anti-CTGF agent used in the methods of the present invention may, for example, be a polypeptide, polynucleotide, or small molecule. In particular, the anti-CTGF agent may be an antibody that binds to CTGF, or a fragment thereof, an antisense molecule; a siRNA; or a small molecule chemical compound. In specific embodiments, the anti-CTGF agent is a monoclonal antibody directed against CTGF, or a fragment thereof. In other specific embodiments, the anti-CTGF agent is CLN-1, described in WO 2004/108764, or a fragment thereof.

DESCRIPTION OF THE INVENTION

It is to be understood that the invention is not limited to the particular methodologies, protocols, cell lines, assays, and reagents described herein, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments, a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley &

Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The present invention relates in part to the discovery that connective tissue growth factor (CTGF) plays a key role in specific aspects of cardiovascular disease, including impaired vascular function (i.e., vascular dysfunction) and impaired cardiac function (i.e., cardiac dysfunction).

The present invention is based in part on the discovery of unexpected benefits of inhibition of CTGF in treatment of multiple and specific aspects of vascular dysfunction and cardiac dysfunction. The present invention provides data demonstrating that inhibition of CTGF reduced various pathological aspects of cardiovascular disease not previously associated with CTGF. In certain aspects, the present invention provides evidence that inhibition of CTGF provides a therapeutic approach to treat or prevent specific physiological and pathological aspects of vascular dysfunction and cardiac dysfunction.

The present invention provides methods and agents for reducing, ameliorating, or reversing in a subject complications associated with multiple, distinct pathological processes associated with impaired vascular function and impaired cardiac function. In some embodiments, the subject is an animal, more preferably a mammal, and most preferably a human.

The present invention also provides agents for use in the methods described herein. Such agents may include small molecule compounds; peptides and proteins including antibodies or functionally active fragments thereof; and polynucleotides including small interfering ribonucleic acids (siRNAs), micro-RNAs (mRNAs), ribozymes, and anti-sense sequences. (See, e.g., Zeng (2003) Proc Natl Acad Sci USA 100:9779-9784; and Kurreck (2003) Eur J Biochem 270: 1628-1644.)

Impaired Vascular Function

Impaired vascular function (e.g., vascular dysfunction) can result from various abnormalities, including, for example, disturbance or impairment of the structure and/or function of the vasculature. Impaired vascular function is associated with various pathologies and damage to the vasculature, resulting in deleterious changes leading to, for example, arterial stiffness, vascular permeability, and vascular calcification.

Arterial stiffness encompasses properties such as vascular distensibility, compliance, and elastic modulus and has been shown to be a good predictor of coronary heart disease and cardiovascular mortality. (See, e.g., O'Rouke et al (2002) Am J Hypertens 15:426-444; Boutouyrie et al (2002) Hypertension 39:10-15; Blacher et al (1999) Circulation 99:2434-2439.) In general, increased arterial stiffness can lead to increased systolic pressure, increased ventricular mass, and decreased diastolic coronary perfusion. Increased arterial stiffness has also been associated with reduced flow volume in the lower-extremity arteries. (See, e.g., Suzuki et al (2001) Diabetes Care 24:2107-2114.)

Increased arterial stiffness, i.e., arterial stiffening, is associated with many disease states, including diabetes and chronic kidney disease, and is a hallmark of the aging process. Arterial stiffening is of particular concern in individuals with diabetes or metabolic syndrome, in which arterial stiffening is consistently observed across all age groups. Arterial stiffening is also a marker for increased risk for cardiovascular disease, including, for example, myocardial infarction, heart (i.e., cardiac) failure, total mortality, stroke, dementia, and renal disease.

Arterial stiffening is associated with deleterious effects on the structure and function of both the vasculature and the heart. In arteries, arterial stiffening affects changes in mechanical vascular stimulation, leading to endothelial dysfunction and vascular disease. In the heart, arterial stiffening influences the work load imposed on the ventricles, the efficiency of cardiac ejection, and the perfusion of the heart itself.

Clinical surrogate markers for arterial stiffening include isolated systolic hypertension and increased pulse pressure. Pulse pressure is the difference between systolic blood pressure and diastolic blood pressure. Arterial stiffness is associated with increased pulse pressure. Increased pulse pressure values above normal values are indicative of arterial stiffening. Arterial stiffness can also be assessed by measurement of pulse wave velocity (PWV). (See, e.g., Lehman et al (1992) Diabetic Med 9:114-119.) Pulse wave velocity is the velocity of travel of the ventricular ejection pressure wave traveling away from the heart along a length of an artery. The velocity of the pulse wave along an artery is dependent on the stiffness of that artery. Pulse wave velocity measurements are often performed between the carotid artery and femoral artery. Slower waves indicate arterial plasticity, while faster waves indicate arterial stiffness; therefore, the higher the pulse wave velocity, the higher the rigidity and stiffness of the vascular wall and the lower the distensibility. (See, e.g., Nichols and O'Rourke in McDonald's blood flow in arteries. Theoretical, experimental and clinical principles. Fourth Edition, London, Sydney, Auckland: Arnold E. 1998.) These and other methods for determining arterial stiffness are well known in the art and are readily available to one of skill in the art.

Vascular calcification, including coronary calcification, valvular calcification, aortic calcification, and arterial calcification, has direct effects on both vascular function and cardiac function. Vascular calcification is associated with stiffening and dilation of the walls of the large blood vessels, such as the aorta and common carotid artery, and affects vascular function by impairing contraction and relaxation of blood vessels. Vascular calcification is an established indicator of coronary disease and vascular disease, and plays a crucial role in development and pathogenesis of cardiovascular disease, including impaired vascular function and impaired cardiac function, and, as such, is associated with a higher risk of myocardial infarction and death. (See, e.g., Doherty et al (2004) Endocr Rev 25:629-627.) Vascular calcification can occur in both the intima and the media of arteries.

The present invention provides methods and agents useful for treating impaired vascular function. In various embodiments, methods and agents of the present invention are useful for treating impaired vascular function, wherein the impaired vascular function is arterial stiffness, vascular permeability, extravasation, and vascular calcification.

In certain aspects, the present invention relates to methods for reducing vascular dysfunction and improving vascular function in a subject having or at risk for having diabetes. Additionally, the present invention relates to methods for reversing vascular complications, pathologies, or damage associated with diabetes or elevated blood glucose levels in a subject having or at risk for having diabetes. It is specifically contemplated that, in preferred embodiments of each of the methods described below, the preferred subject is a human subject.

The present invention provides a method for reducing vascular dysfunction in a subject having or at risk for having diabetes, the method comprising administering to the subject an effective amount of an anti-CTGF agent, thereby reducing vascular dysfunction in the subject. An anti-CTGF agent, as the term is used herein, is any agent that inhibits the expression or activity of CTGF. A method for improving vascular function in a subject having or at risk for having diabetes, the method comprising administering to the subject an effective amount of an anti-CTGF agent, thereby improving vascular function, is also provided herein.

The present invention provides a method for reversing vascular complications, pathology, or damage in a subject having or at risk for having vascular complications, pathology, or damage associated with diabetes, the method comprising administering to the subject an effective amount of an anti-CTGF agent, thereby reversing vascular complications, pathology, or damage in the subject.

As certain methods described herein refer to a subject having or at risk for having diabetes, it is contemplated that whether the subject is a subject that has or is at risk for having diabetes can be determined by any measure accepted and utilized by those of skill in the art. For example, a human subject having a blood glucose level above about 200 mg/dL (e.g., as determined in a fasting blood glucose test, an oral glucose tolerance test, or a random blood glucose test) may be characterized as a subject having diabetes. Therefore, in certain aspects, it is contemplated that a human subject having a blood glucose level above about 200 mg/dL is a suitable subject for treatment with the methods of or use of medicaments provided by the present invention. A subject at risk for having diabetes, for example, a human subject at risk for having diabetes, can be identified by an assessment of one or more of various factors known to be associated with an increased risk of developing diabetes, including family history of diabetes, certain ethnic or racial groups, a history of gestational diabetes, obesity, in particular, high levels of visceral or abdominal fat, a sedentary lifestyle, age, high blood pressure, schizophrenia, etc., as well as altered glucose metabolism, including impaired glucose tolerance (IGT) or prediabetes.

In various embodiments of the present methods, the vascular dysfunction is microvascular dysfunction or is macrovascular dysfunction. In certain embodiments, the dysfunction is cardiovascular dysfunction, or cerebrovascular dysfunction, or vascular dysfunction associated with nephropathy, retinopathy, or neuropathy. In a particular embodiment, the dysfunction is ventricular dysfunction, and, in a further embodiment, left ventricular dysfunction. In one embodiment, the dysfunction is dysfunction of the peripheral vasculature.

Methods for improving vascular function are also encompassed by the present invention. In one aspect, the invention provides a method for improving vascular function in a subject having or at risk for having diabetes, the method comprising administering to the subject an effective amount of an anti-CTGF agent, thereby improving vascular function in the subject.

It is contemplated in various aspects that the vascular function is microvascular function or is macrovascular function. In certain embodiments, the vascular function is cardiovascular or is cerebrovascular, or is associated with nephropathy, retinopathy, or neuropathy. In a certain aspect, the function is ventricular function, and, in a further aspect, left ventricular function. In one aspect, the vascular function is associated with the peripheral vasculature.

The invention further encompasses a method for reducing endothelium dysfunction in a subject having or at risk for having diabetes, the method comprising administering to the subject an effective amount of an anti-CTGF agent, thereby reducing endothelium dysfunction in the subject. A method for improving endothelium function in a subject having or at risk for having diabetes, the method comprising administering to the subject an effective amount of an anti-CTGF agent, thereby improving endothelium function, is also provided herein. Methods for reversing endothelium dysfunction are specifically contemplated by the present invention.

In one embodiment, the present invention provides a method for treating a vascular complication associated with diabetes in a subject having or at risk for having diabetes, the method comprising administering to the subject an anti-CTGF agent, thereby treating the vascular complication. An anti-CTGF agent is any agent that inhibits the activity and/or the expression of CTGF. Methods for reducing the progression or severity of a vascular complication in a subject having or at risk for having diabetes, the methods comprising administering to the subject an effective amount of an anti-CTGF agent, thereby reducing the progression or severity of the vascular complication, are also provided. Further contemplated herein are methods of preventing or slowing the development of a vascular complication in a subject having or at risk for having diabetes, the method comprising administering to the subject an effective amount of an anti-CTGF agent, thereby preventing or slowing the development of the vascular complication. In another embodiment, the present invention provides a method for reversing vascular complications, pathology, or damage associated with diabetes in a subject having or at risk for having vascular complications, pathology, or damage associated with diabetes, the method comprising administering to the subject an effective amount of an anti-CTGF agent, thereby reversing vascular complications, pathology, or damage associated with diabetes in the subject.

In certain embodiments, the vascular complication is a macrovascular complication; in other embodiments, a microvascular complication. In various embodiments, the complication is selected from the group consisting of a cardiopathy, a nephropathy, a neuropathy, and a retinopathy. In one embodiment, the complication is a cardiovascular complication or a cerebrovascular complication. In another embodiment, the complication is a complication of the peripheral vasculature.

Further methods are provided herein, including methods for treating arterial stiffness, the methods comprising administering to a subject having or at risk for having diabetes an effective amount of an anti-CTGF agent, thereby treating arterial stiffness. In various aspects, the arterial stiffness is selected from the group consisting of axial, radial, and circumferential arterial stiffness. Methods for reducing vascular permeability; reducing extravasation, e.g., edema, or tissue edema; reducing intima-media thickening; and reducing common carotid artery intima-media thickening are encompassed by the present invention. In each case, the method comprises administering to a subject having or at risk for having diabetes an effective amount of an anti-CTGF agent, thereby achieving the desired effect, e.g., reducing vascular permeability; reducing extravasation, e.g., edema, or tissue edema; reducing intima-media thickening; and reducing common carotid artery intima-media thickening, respectively.

In one aspect, the invention contemplates a method for reducing damage to or dysfunction of blood vessels in a subject having or at risk for having diabetes, the method comprising administering to a subject having or at risk for having diabetes an effective amount of an anti-CTGF agent, thereby reducing damage to or dysfunction of blood vessels in the subject. In various aspects, the blood vessels can be blood vessels of the macrovasculature, e.g., major blood vessels such as the aorta, the coronary arteries, the carotid arteries, the cerebrovascular arteries, the renal arteries, the iliac arteries, the femoral arteries, the popliteal arteries, or can be blood vessels of the microvasculature, e.g., small blood vessels such as the retinal arterioles, the glomerular arterioles, the vasa nervorum, the cardiac arterioles, and associated capillary beds of the eye, the kidney, the heart, and the central and peripheral nervous system.

In one aspect, the invention provides a method for reducing vascular calcification in a subject, the method comprising administering to the subject an effective amount of an anti-CTGF agent, thereby reducing vascular calcification in the subject. In certain aspects, as in the methods described above, the subject is a subject having or at risk for having diabetes.

In a preferred embodiment, the subject is a mammalian subject, and in a most preferred embodiment, the subject is a human subject. In certain embodiments, the subject is a subject having or at risk for having diabetes.

Impaired Cardiac Function

Impaired cardiac function (e.g., cardiac dysfunction) and heart disease can result from various abnormalities, including, for example, disturbance or impairment of the contraction and/or of the relaxation of the heart and myocardium. From a clinical point of view, impaired cardiac function may be considered as any condition in which an abnormality of cardiac function is responsible for the inability of the heart to pump blood at a rate commensurate with the requirements of the metabolizing tissues and/or allows it to do so only from an abnormally elevated ventricular diastolic volume. Impaired cardiac function (e.g., cardiac dysfunction, heart failure) can be systolic cardiac dysfunction or diastolic cardiac dysfunction, also known as systolic heart failure and diastolic heart failure, respectively.

In systolic cardiac dysfunction, the principal abnormality is the inability of the ventricle to contract normally and expel sufficient blood. Systolic cardiac dysfunction is associated with an impairment of myocardial contractility, which causes weakened systolic contraction, leading to a reduction in stroke volume and cardiac output, inadequate ventricular emptying, cardiac dilatation, and often elevation of ventricular diastolic pressure. Systolic cardiac dysfunction in adult humans is defined as a left ventricular ejection fraction of less than 45%. In diastolic cardiac dysfunction, the principal abnormality is the inability of the ventricle to relax and/or fill normally. Impaired relaxation and filling of the ventricle associated with diastolic cardiac failure leads to an elevation of ventricular diastolic pressure at any given diastolic volume. Many patients with impaired cardiac function exhibit abnormalities of both ventricular contraction and ventricular relaxation.

Several techniques are available to one of skill in the art for identifying, diagnosing, or otherwise assessing impaired cardiac function in a subject. Generally, such techniques include, for example, electrocardiography, echocardiography, cardiac catheterization, angiography, and nuclear imaging cardiology techniques, including radionuclide angiography.

In some instances, with the subject at rest, and at normal or elevated ventricular end-diastolic pressure, the cardiac output and stroke volume may be depressed in the presence of heart dysfunction or heart failure. In many instances, cardiac function that may be adequate at rest may be inadequate during exertion.

Cardiac function is often assessed by determining the ejection fraction, a measurement of the fraction of blood pumped out of the heart during each beat. Ejection fraction is the ratio of stroke volume to end-diastolic volume, and is calculated by dividing the volume of blood ejected from a ventricle (called the stroke volume, SV) by the volume of blood in the ventricle after filling (end-diastolic volume, EDV). A normal value for ejection fraction in adult human subjects is 50-70%. Damage to the heart impairs the heart's ability to eject blood effectively and therefore reduces ejection fraction. Reduction in ejection fraction can manifest clinically as cardiac dysfunction or heart failure. Ejection fraction is one of the most important predictors of prognosis associated with cardiac dysfunction; subjects with reduced ejection fractions typically have a poorer prognosis.

Ejection fraction is commonly measured by echocardiography, in which the volumes of the heart's chambers (e.g., ventricles) are measured during the cardiac cycle. Ejection fraction can also be measured using cardiac MRI, fast scan cardiac axial tomography (CT) imaging, ventriculography, gated SPECT, and radiocontrast or radionucleotide angiography.

A normal left ventricle ejects 50-80% of its end-diastolic volume with each beat; i.e., its ejection fraction is 0.50 to 0.80. In human adults, normal values for left ventricular volumes are as follows: end-diastolic volume of 72+/−15 mL/m2 (mean+/−standard deviation) and end-systolic volume of 20+/−8 mL/m2.

The invention encompasses additional methods, including methods for improving cardiac function; improving ventricular relaxation; improving ventricular contractility; improving end diastolic pressure; improving end diastolic volume; improving ejection fraction; improving arterial elastance; improving stroke volume; and improving cardiac output, respectively. Each of these methods comprises administering to a subject having or at risk for having diabetes an effective amount of an anti-CTGF agent, thereby achieving the desired effect, e.g., improving cardiac function; improving ventricular relaxation; improving ventricular contractility; improving end diastolic pressure; improving end diastolic volume; improving ejection fraction; improving arterial elastance; improving stroke volume; and improving cardiac output in the subject, respectively.

In one embodiment, the present invention provides a method for treating or preventing a cardiac complication, the method comprising administering to the subject an anti-CTGF agent, thereby treating or preventing the cardiac complication. In certain embodiments, the subject is a subject having or at risk for having diabetes. In particular, the present methods can be used for treating or preventing a cardiac complication selected from cardiohypertrophy, congestive heart failure and cardiomyopathy. The present methods can also be for treating or preventing a cardiac complication by reducing blood LDL levels.

In a preferred embodiment, the subject is a mammalian subject, and in a most preferred embodiment, the subject is a human subject. In certain embodiments, the subject is a subject having or at risk for having diabetes.

Anti-CTGF Agents

In any of the methods described above, it is particularly contemplated that the anti-CTGF agent may be a polypeptide, polynucleotide, or small molecule; for example, an antibody that binds to CTGF, an antisense molecule, siRNAs, small molecule chemical compounds, etc. In particular, the present invention contemplates that inhibiting CTGF can be accomplished by any of the means well-known in the art for modulating the expression and activity of CTGF. Use of anti-CTGF agent, for example, a human monoclonal antibody directed against CTGF, is preferred, although any method of inhibiting expression of the gene encoding CTGF, inhibiting production of CTGF, or inhibiting activity of CTGF is contemplated by the present invention.

Exemplary antibodies for use in the methods of the present invention are described, e.g., in U.S. Pat. No. 5,408,040; International Publication No. WO 99/07407; International Publication No. WO 99/33878; and International Publication No. WO 00/35936. An exemplary antibody for use in the methods of the present invention is described in International Publication No. WO 2004/108764, incorporated by reference herein in its entirety. Such antibodies, or fragments thereof, can be administered by various means known to those skilled in the art. For example, antibodies are often injected intravenously, intraperitoneally, or subcutaneously.

Small molecule inhibitors of CTGF expression and/or activity have also been described; for example, International Publication No. WO 96/38172 identifies modulators of cAMP such as cholera toxin and 8Br-cAMP as inhibitors of CTGF expression. Therefore, compounds identified as, e.g., prostaglandin and/or prostacyclin analogs such as Iloprost (see, e.g., International Publication No. WO 00/02450; Ricupero et al. (1999) Am J Physiol 277:L1165-1171; also, see Ertl et al. (1992) Am Rev Respir Dis 145:A19), and potentially phosphodiesterase IV inhibitors (see, e.g., Kohyama et al. (2002) Am J Respir Cell Mol Biol 26:694-701), may be used to modulate CTGF expression. Also, inhibitors of serine/threonine mitogen activated protein kinases, particularly p38, cyclin-dependent kinase, e.g. CDK2, and glycogen synthase kinase (GSK)-3 have also been implicated in decreased CTGF expression. (See, e.g., Matsuoka et al. (2002) Am J Physiol Lung Cell Mol Physiol 283:L103-L112; Yosimichi et al. (2001) Eur J Biochem 268:6058-6065; International Publication No. WO 01/38532; and International Publication No. WO 03/092584.) Such compounds can be formulated and administered according to established procedures within the art.

Further, polynucleotides including small interfering ribonucleic acids (siRNAs), micro-RNAs (mRNAs), ribozymes, and anti-sense sequences may be used in the present methods to inhibit expression and/or production of CTGF. (See, e.g., Kondo et al. (2000) Biochem Biophys Res Commun 278: 119-124.) Such techniques are well-known to those of skill in the relevant art. Anti-sense constructs that target CTGF expression have been described and utilized to reduce CTGF expression in various cell types. (See, e.g., International Publication No. WO 96/38172; International Publication No. WO 00/27868; International Publication No. WO 00/35936; International Publication No. WO 03/053340; Kothapalli et al. (1997) Cell Growth Differ 8(1):61-68; Shimo et al. (1998) J Biochem (Tokyo) 124(1):130-140; and Uchio et al. (2004) Wound Repair Regen 12:60-66.) Such antisense constructs can be used to reduce expression of CTGF and thereby ameliorate or prevent the pathological processes induced by CTGF. Such constructs can be designed using appropriate vectors and expressional regulators for cell- or tissue-specific expression and constitutive or inducible expression. Such genetic constructs can be formulated and administered according to established procedures within the art.

Accordingly, in certain embodiments of the present invention, the anti-CTGF agent is an antibody to CTGF. In a preferred embodiment, the antibody is a monoclonal antibody to CTGF. In another preferred embodiment, the antibody is a human or humanized antibody to CTGF. In a particular embodiment, the antibody is CLN-1, as described in International Publication No. WO 2004/108764. In another embodiment, the agent is a small molecule. In another embodiment, the agent is a nucleic acid. In a further embodiment, the nucleic acid is selected from the group consisting of a cyclic nucleotide, an oligonucleotide, or a polynuycleotide. In particular embodiments, the agent is an antisense oligonucleotide or an siRNA.

The present invention contemplates the use of the present methods in combination with other therapies. In one embodiment, the method is used in combination with another therapy, e.g., to further augment therapeutic effect on certain pathological events, etc. The two treatments may be administered at the same time or consecutively, e.g., during a treatment time course or following disease progression and remission. In another embodiment, the method is used in combination with another therapeutic method having a similar or different mode of action, e.g., an ACE inhibitor, ARBs, statin, advanced glycation endproduct (AGE) inhibitor, etc. Current therapeutic approaches to treat vascular complications and disease are known by one of skill in the art, and include, for example, ACE inhibitors, angiotensin receptor blockers, statins, advanced glycation endproduct inhibitors, calcium channel blockers, etc. Use of any of these therapeutic agents in combination with the use of methods of the present invention is specifically contemplated.

Bradykinin has been shown to regulate the expression of CTGF, and bradykinin B1 receptor antagonists reduced vascular permeability in diabetic animals. (See, e.g., Ricupero et al. (2000) J Biol Chem 275:12475-12480; Lawson et al. (2005) Regul Pept 124:221-224; Tan et al. (2005) Am J Physiol Renal Physiol 288:F483-F492; Wilkinson-Berka and Fletcher (2004) Curr Pharm Des 10:3313-3330.) Therefore, in certain aspects, the present invention provides methods and agents for regulating the kallikrien-kinin system to modulate CTGF-mediated vascular complications, such as, for example, vascular permeability and extravasation. Use of agents and methods that regulate the kallikrien-kinin system, alone or in combination with the use of agents and methods that inhibit CTGF, is specifically contemplated.

Pharmaceutical Formulations and Routes of Administration

The compositions of the present invention can be delivered directly or in pharmaceutical compositions containing excipients, as is well known in the art. Present methods of treatment can comprise administration of an effective amount of a compound of the present invention to a subject having or at risk for having vascular dysfunction (i.e., impaired vascular function) or cardiac dysfunction (i.e., impaired cardiac function). In a preferred embodiment, the subject is a mammalian subject, and in a most preferred embodiment, the subject is a human subject.

An effective amount, e.g., dose, of compound or drug can readily be determined by routine experimentation, as can an effective and convenient route of administration and an appropriate formulation. Various formulations and drug delivery systems are available in the art. (See, e.g., Gennaro, ed. (2000) Remington's Pharmaceutical Sciences, supra; and Hardman, Limbird, and Gilman, eds. (2001) The Pharmacological Basis of Therapeutics, supra.)

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., USP, JP, EP, and BP, FDA web page (www.fda.gov), Inactive Ingredient Guide 1996, and Handbook of Pharmaceutical Additives, ed. Ash; Synapse Information Resources, Inc. 2002.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include, fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons dervided from methan and ethan, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

For composition useful for the present methods of treatment, a therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

A therapeutically effective dose or amount of a compound, agent, or drug of the present invention refers to an amount or dose of the compound, agent, or drug that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the agent or pharmaceutical composition that will elicit the biological or medical response of a tissue, system, animal, or human that is being sought by the researcher, veterinarian, medical doctor, or other clinician, e.g., improved vascular function, improved cardiac function, etc.

Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects, e.g., improved vascular function, improved cardiac function, etc, i.e., minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications are intended to fall within the scope of the appended claims.

Example 1

Anti-CTGF Therapy Improves Hemodynamic Parameters and Cardiac Function

The methods of the invention were used to demonstrate broad-spectrum efficacy in an animal model for certain aspects of vascular complications associated with diabetes as follows. Diabetes mellitus was induced in Sprague Dawley rats by a single i.v. dose of streptozotocin (STZ) (65 mg/kg). STZ-induced diabetes in rats leads to increased vascular permeability (Lawson et al. (2005) Regul Pept 124:221-224) and decreased cardiac function (Machackova et al. (2004) Mol Cell Biochem 261:271-278). Experimental rats received an intravenous injection of 0.1M citrate-buffered streptozotocin (pH 4.1) at a dosage of 65 mg/kg (65 mg/ml) on day zero. Successful induction of diabetes in animals treated with STZ was confirmed on day 2 by an elevation in fasted blood glucose levels (>250 mg/dl).

Diabetic animals were divided into treatment groups (Vehicle, 3 mg/kg, 5 mg/kg, or 10 mg/kg anti-CTGF antibody, CLN-1). Treated animals received vehicle or anti-CTGF antibody by IP injection three times per week for six weeks. At the end of six weeks, animals were anesthetized and a microtip conductance catheter with pressure transducer (Millar instruments) was placed in the left ventricle for measurement of cardiac function. Pressure volume loops were recorded by a computerized data acquisition system (ADI Instruments). Hemodynamic parameters were determined by computer analysis of pressure volume loops (PVAN system, Millar Instruments). Alternately, animals were lightly anesthetized and cardiac function was measured using cardiac ultrasound techniques. Such techniques are readily known to one skilled in the art.

Diabetic animals showed reduced cardiac function, as determined by various hemodynamic and cardiac function parameters. Diabetic animals treated with anti-CTGF antibody showed increased cardiac function compared to non-treated diabetic animals. Specifically, diabetic animals treated with anti-CTGF antibody showed improved ventricular relaxation, ventricular contractility, end diastolic pressure, end diastolic volume, ejection fraction, arterial elastance, stroke volume, and cardiac output. Taken together, these results indicated that inhibition of CTGF provides a therapeutic approach for treating vascular complications, such as improving cardiac and vascular function, associated with diabetes.

Diabetic animals showed reduced cardiac function, as determined by various hemodynamic and cardiac function parameters. The effect of anti-CTGF therapy on ejection fraction, which is stoke volume divided by total volume, was examined. As shown in FIG. 1, diabetic animals had impaired or reduced systolic and diastolic function. In particular, diabetic animals had reduced percent ejection fraction (EF) compared to that of healthy control animals. Diabetic animals administered anti-CTGF antibody showed an increase in percent ejection fraction compared to non-treated control diabetic animals. (See FIG. 1.) Following administration of anti-CTGF antibody (from week 6 to week 12), diabetic animals had a percent ejection fraction similar to/comparable to the percent ejection fraction observed in healthy non-diabetic control animals. This data showed that anti-CTGF antibody administration prevented decreases in ejection fraction.

Figure 2:
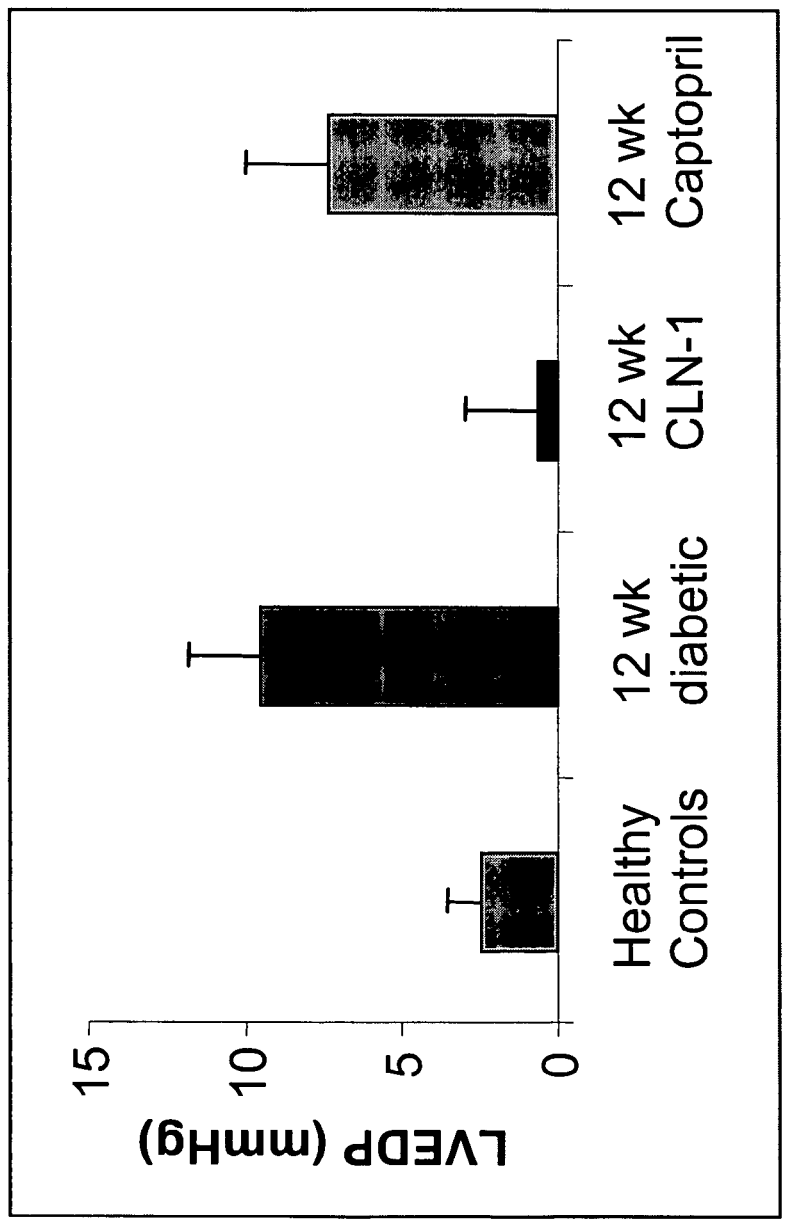
FIG. 2 shows the present methods and agents effectively reduced left ventricular end-diastolic pressure in mammalian subjects.

The effect of anti-CTGF therapy on Left ventricular end diastolic pressure (LVEDP) was also examined. Diabetic animals showed increased left ventricular end diastolic pressure. As shown in FIG. 2, administration of anti-CTGF antibody prevented the increase in left ventricular end diastolic pressure observed in non-treated control diabetic animals. Diabetic animals administered anti-CTGF antibody had a left ventricular end diastolic pressure similar to that observed in non-diabetic healthy control animals. These results indicated that anti-CTGF antibody administration prevented increases in left ventricular end diastolic pressure.

Figure 3:
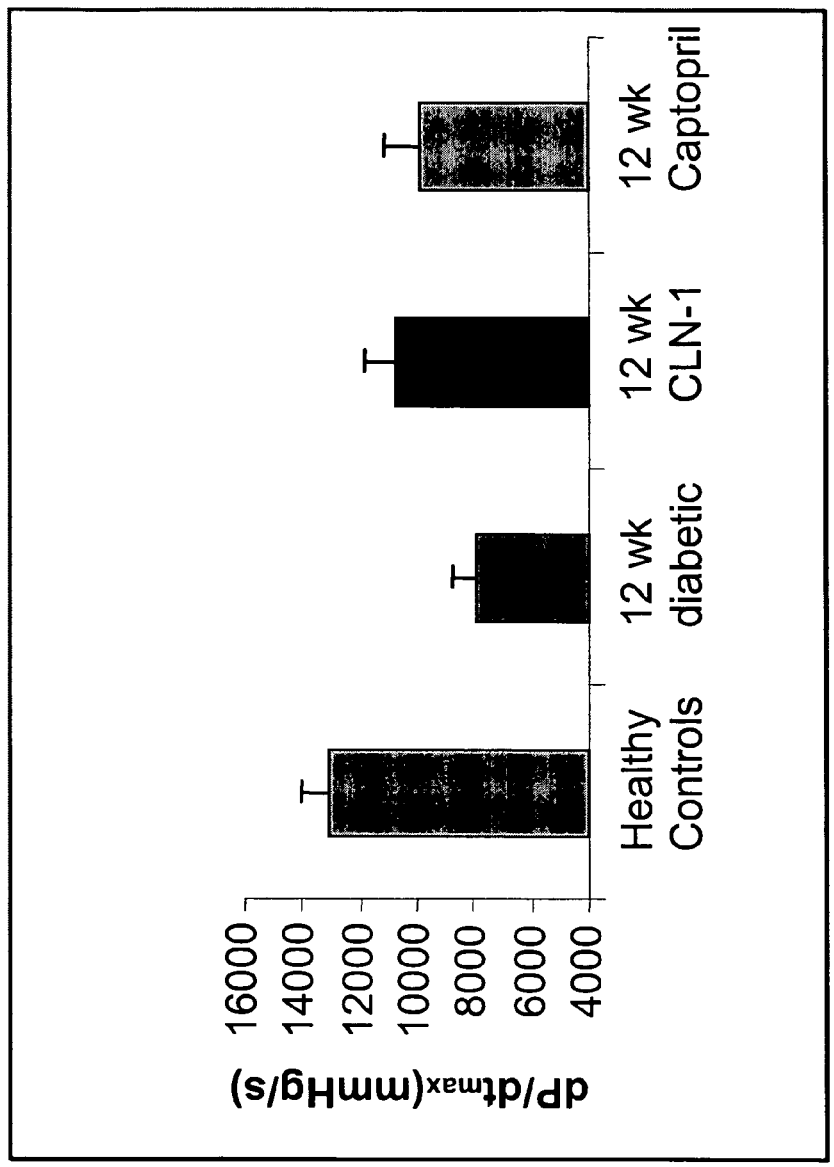
FIG. 3 shows the present methods and agents effectively improved cardiac contractility in mammalian subjects.
Figure 4:
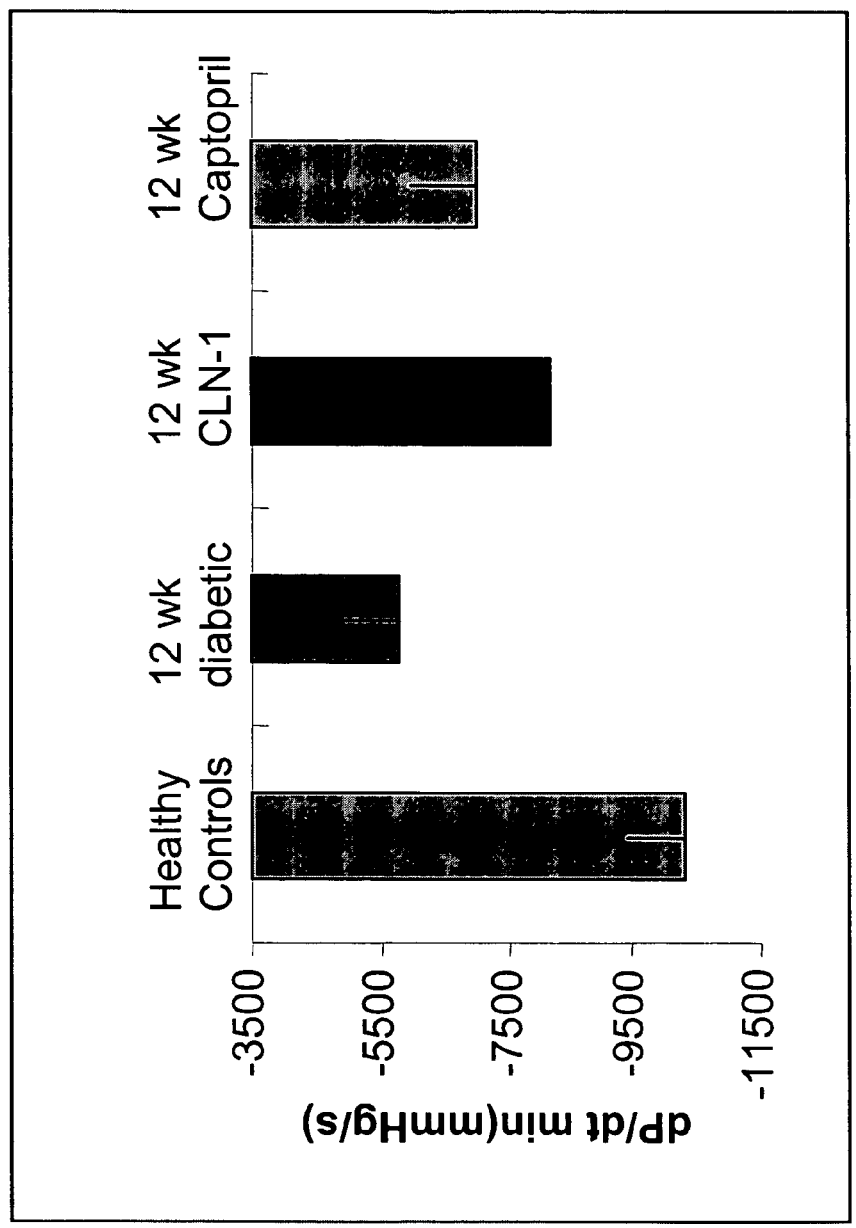
FIG. 4 shows the present methods and agents effectively improved the rate of cardiac relaxation of the ventricle in mammalian subjects.

The effects of anti-CTGF therapy on cardiac contractility and relaxation were also examined. As shown in FIG. 3, diabetic animals showed a reduction in dP/dt maximum compared to non-diabetic healthy control animals. Additionally, administration of anti-CTGF antibody to diabetic animals prevented the decrease in dP/dt minimum contractility observed in non-treated diabetic animals. (See FIG. 4.) Reduction of dP/dt maximum and reduction in the decrease of dP/dt minimum is indicative of improvement in cardiac contractility and relaxation.

Taken together, these results showed that anti-CTGF therapy is effective at improving cardiac function.

Example 2

Anti-CTGF Therapy Reduces Arterial Stiffness

The effect of anti-CTGF therapy on arterial stiffness (a measure of vascular function, and in particular macrovascular function) was measured using the animal model of diabetes described above in Example 1. Various measurements of arterial stiffness were obtained, including passive and active pressure-volume data from the carotid artery. For these measurements, the distal portion of the left carotid artery was cannulated with PE-50 tubing connected to a three-way stopcock. A modified Krebs buffer solution was infused into the carotid artery via the cannula. The proximal end of the carotid artery was occluded using a vascular occluder. To measure force developed during infusion of the buffer solution, a pressure transducer was connected to the three-way stopcock. The PE-tubing end was also connected to an isometric force transducer to measure the isometric axial force during pressurization. A digital image analysis system was used to measure changes in outer radii of the arterial segment. Passive arterial stiffness was determined by perfusing the arterial segment with $Ca^{2+}$-free buffer. To measure active stiffness of the arterial wall, vasodilators and vasoconstrictors such as norepinephrine were added to the perfusate. In certain experiments, arterial segments were removed from the animal and evaluated ex vivo at in vivo stretch length with a similar apparatus.

Figure 5:
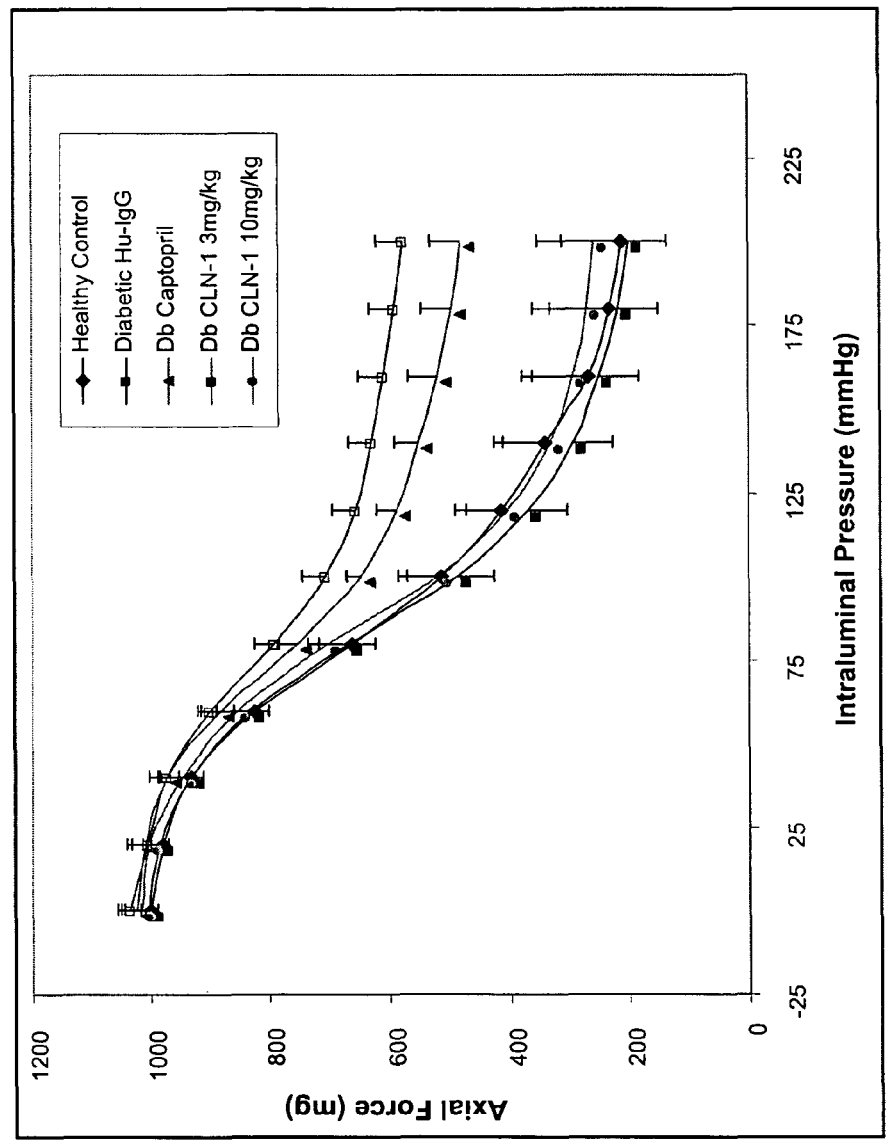
FIG. 5 shows the present methods and agents effectively reduced axial stiffness of carotid arteries in mammalian subjects.

Diabetic rats had increased arterial stiffness of the carotid artery. As shown in FIG. 5, force-pressure curves of isolated carotid arteries demonstrated increased axial stiffness of the carotid arteries in diabetic animals. Axial stiffness of the carotid arteries of diabetic animals treated with either 3 mg/kg or 10 mg/kg anti-CTGF antibody (CLN-1) was similar to that of healthy control animals. These results showed that treatment of diabetic animals with anti-CTGF antibody prevented or reduced axial stiffness (e.g., prevented or reduced vascular dysfunction, and in particular, prevented or reduced macrovascular dysfunction) of the carotid artery, and that treatment with anti-CTGF antibody normalized axial stiffness associated with diabetes to that of non-diabetic controls.

Figure 6:
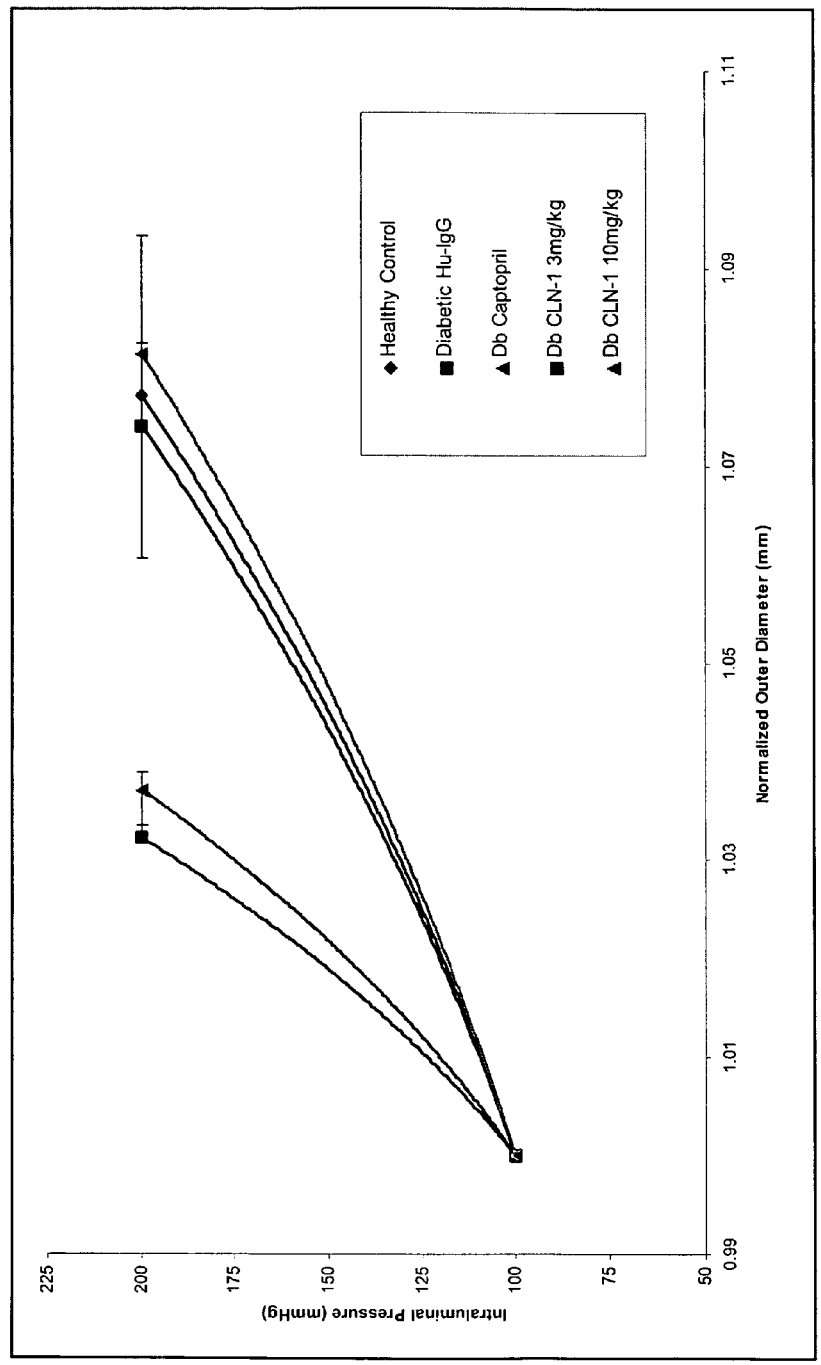
FIG. 6 shows the present methods and agents effectively reduced circumferential stiffness of carotid arteries in mammalian subjects.

Additionally, analysis of pressure radius curves indicated that diabetic animals displayed increased circumferential (i.e., radial) stiffness of the carotid arteries. Diabetic animals treated with anti-CTGF antibody showed carotid artery circumferential stiffness similar to that of non-diabetic animals. (See FIG. 6.)

Taken together, these data showed inhibition of CTGF provided a method to reduce or prevent an increase in arterial and vascular stiffness associated with diabetes. Therefore, inhibition of CTGF provides a therapeutic approach for treating vascular complications associated with diabetes and for improving vascular function.

In addition to the above-described experiments, the methods and agents of the present invention were used to demonstrate broad-spectrum efficacy in an animal model for additional aspects of vascular complications associated with diabetes. In one series of experiments, the effect of anti-CTGF therapy on arterial stiffness (a measure of vascular function, and in particular macrovascular function) was measured using the animal model of diabetes described above in Example 1. Diabetes (type 1 diabetes) was induced in Sprague Dawley rats by a single i.v. injection of 0.1 M citrate-buffered (pH 4.1) streptozotocin (STZ) (65 mg/kg). Successful induction of diabetes in animals treated with STZ was confirmed on day 2 by an elevation in fasted blood glucose levels (>250 mg/dl). STZ-induced diabetes in rats leads to increased vascular permeability (Lawson et al. (2005) Regul Pept 124:221-224).

In another series of experiments, diabetes and disorders associated with diabetes were allowed to progress in the animals for 6 weeks following the STZ injection. After 6 weeks, diabetic animals were then divided into various treatment groups as follows: control human IgG (10 mg/kg, IP injection, three times per week for 6 weeks); anti-CTGF antibody (CLN-1,10 mg/kg, IP injection, three times per week for 6 weeks); Captopril (75 mg/kg/day, PO, in drinking water).

Figure 7:
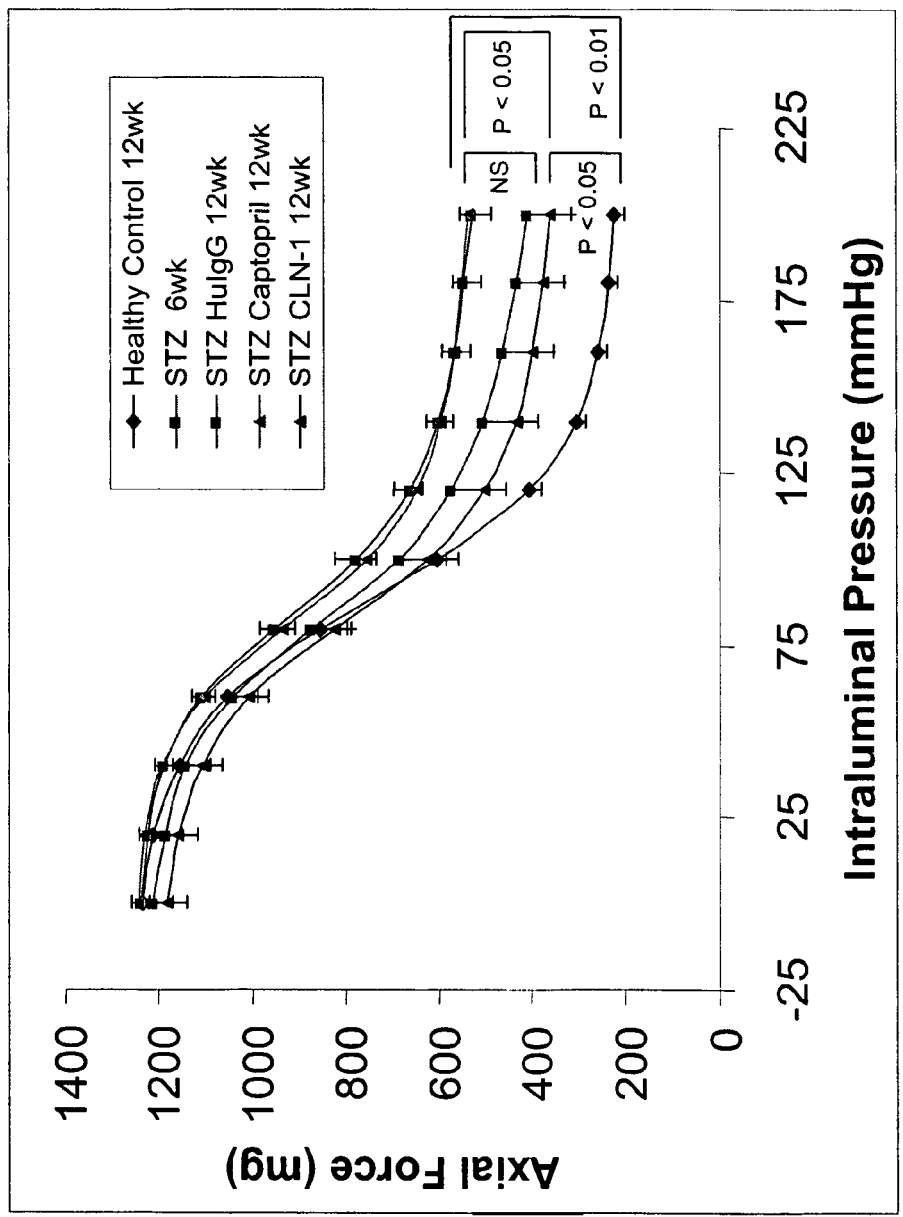
FIG. 7 shows the present methods and agents effectively reduced and reversed axial stiffness of carotid arteries associated with diabetes in mammalian subjects.

FIG. 7 shows the axial force required to maintain the in vivo axial stretch. In FIG. 7, data is presented as mean+/−SE; NS=no significant difference observed; data analyzed by two way ANOVA for repeated measures (Tukey post hoc test).

Diabetic rats had increased arterial stiffness of the carotid artery. Specifically, diabetes significantly increased axial passive stiffness. As shown in FIG. 7, force-pressure curves of isolated carotid arteries demonstrated increased axial stiffness of the carotid arteries in diabetic animals 6 weeks following the induction of diabetes (see STZ 6 wk in FIG. 7). As shown in FIG. 7, increased axial passive stiffness was observed in diabetic animals at 6 weeks (untreated) or in diabetic animals at 12 weeks treated with control HuIgG from week 6 to week 12) compared to axial passive stiffness in non-diabetic control animals. At week 12 following STZ treatment and development of diabetes, animals treated from week 6 to week 12 with control HuIgG displayed increased passive axial stiffness compared to that observed at 6 weeks. These results showed that diabetic animals developed increased arterial stiffness, which progressed and worsened from week 6 through week 12.

Diabetic animals administered anti-CTGF antibody showed a reduction in or had reduced axial passive stiffness compared to diabetic animals administered control HuIgG. (See FIG. 7.) Diabetic animals were administered anti-CTGF antibody beginning 6 weeks following STZ injection and development of diabetes, at which time animals already displayed increased axial stiffness compared to that of non-diabetic animals. Following administration of anti-CTGF antibody from week 6 to week 12, animals had axial passive stiffness measurements lower than that observed at week 6. This data showed that anti-CTGF antibody administration prevented the progression of axial passive stiffness in the carotid artery. This data also indicated that anti-CTGF antibody administration was effective at reversing or reducing axial stiffness associated with diabetes.

These results showed that treatment of diabetic animals with anti-CTGF antibody prevented and reduced axial stiffness (e.g., prevented and reduced vascular dysfunction, and in particular, prevented and reduced macrovascular dysfunction) of the carotid artery, and that treatment with anti-CTGF antibody was effective at reversing axial stiffness associated with diabetes.

Taken together, these data showed inhibition of CTGF provided a method to reduce or prevent an increase in arterial and vascular stiffness associated with diabetes. Therefore, inhibition of CTGF provides a therapeutic approach for treating vascular complications associated with diabetes and for improving vascular function.

Figure 8:
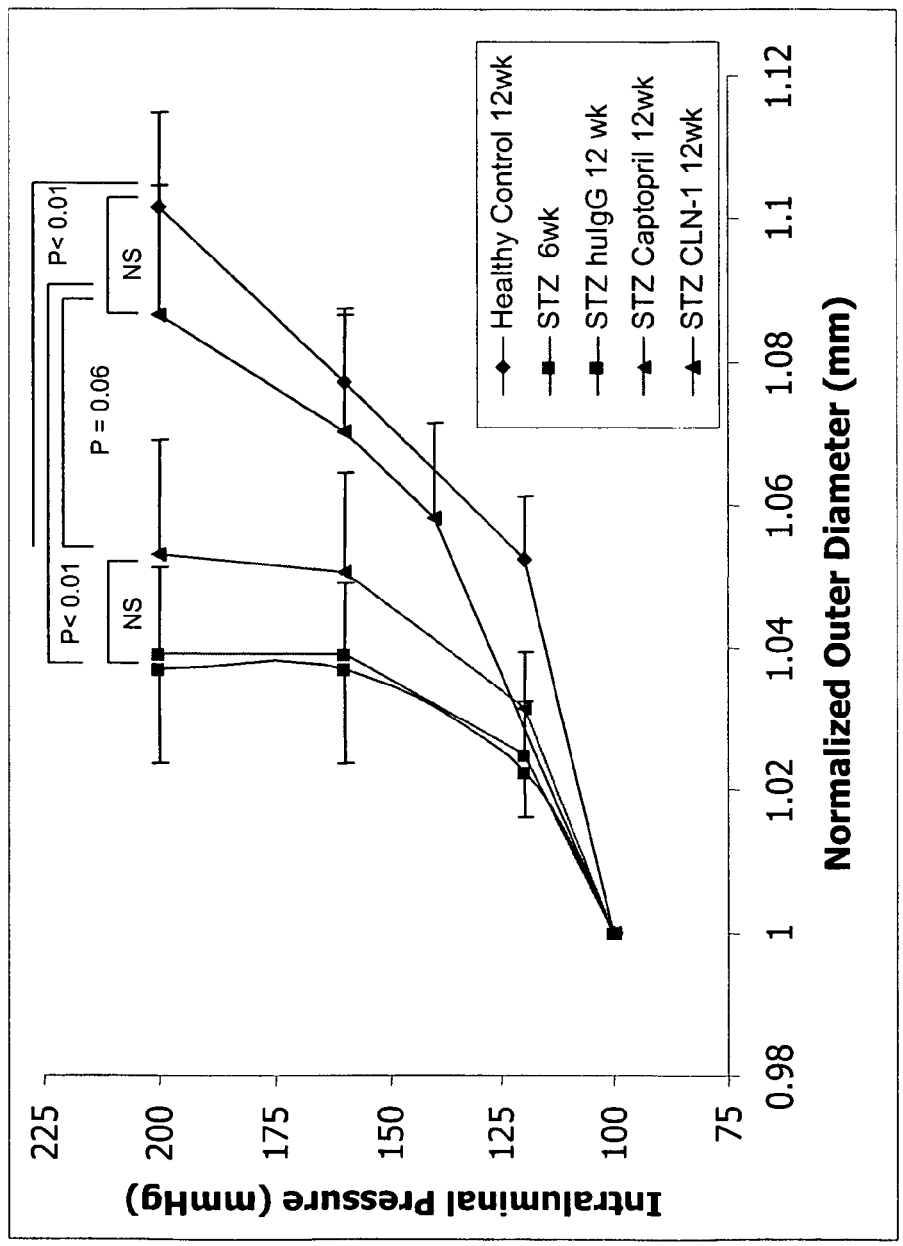
FIG. 8 shows the present methods and agents effectively reduced and reversed circumferential stiffness of carotid arteries associated with diabetes in mammalian subjects.

Additionally, analysis of pressure radius curves in these animals indicated that diabetic animals displayed increased circumferential (i.e., radial) stiffness of the carotid arteries. From FIG. 8, a leftward shift in pressure radius curve at higher pressures indicated increased arterial stiffness. The data showed that diabetic animals at 6 weeks, or diabetic animals treated with control HuIgG from week 6 to week 12 showed increased carotid artery circumferential (i.e., radial) arterial stiffness compared to that of healthy control animals. (See FIG. 8.) In FIG. 8, data is presented as mean+/−SE; NS=no significant difference; data analyzed by ANOVA for repeated measures by LSD post hoc tests.

Diabetic animals treated with anti-CTGF antibody from week 6 through week 12 following STZ injection and development of diabetes showed significantly-reduced carotid artery circumferential stiffness compared to animals treated with control human IgG. These results indicated that administration of anti-CTGF antibody was effective as reducing circumferential arterial stiffness associated with diabetes. Additionally, these results showed that anti-CTGF antibody treatment was effective at reversing and improving (e.g., reducing circumferential arterial stiffness) circumferential passive arterial stiffness associated with diabetes.

Taken together, these data showed that inhibition of CTGF provided a method to reduce, prevent, or reverse increases in arterial and vascular stiffness associated with diabetes (e.g., reduced or reversed vascular dysfunction, in particular, reduced or reversed macrovascular dysfunction). Therefore, inhibition of CTGF provides an effective therapeutic approach for treating vascular complications associated with diabetes and for improving vascular function. Additionally, these results indicated that methods and compounds of the present invention are effective at treating, preventing, reducing, or reversing macrovascular complications associated with diabetes and are thus useful for improving macrovascular function.

Measurement of No-Load and Zero-Stress State

The methods and agents of the present invention were used to demonstrate broad-spectrum efficacy in an animal model for certain aspects of vascular complications associated with diabetes. In one series of experiments, the effect of anti-CTGF therapy on arterial stiffness (a measure of vascular function, and in particular macrovascular function) was measured using an animal model of diabetes as follows. Diabetes (type 1 diabetes) was induced in Sprague Dawley rats by a single i.v. injection of 0.1 M citrate-buffered (pH 4.1) streptozotocin (STZ) (65 mg/kg). Successful induction of diabetes in animals treated with STZ was confirmed on day 2 by an elevation in fasted blood glucose levels (>250 mg/dl).

Diabetes and disorders associated with diabetes were allowed to progress in the animals for 6 weeks following the STZ injection. After 6 weeks, diabetic animals were then divided into various treatment groups as follows: control human IgG (10 mg/kg, IP injection, three times per week for 6 weeks); anti-CTGF antibody (CLN-1, 10 mg/kg, intraperitoneal (IP) injection, three times per week for 6 weeks); Captopril (75 mg/kg/day, PO, in drinking water); Losartan 20 mg/kg/day in drinking water; anti-CTGF antibody (CLN-1, 10 mg/kg, IP injection, three times per week for 6 weeks)+Captopril (75 mg/kg/day, per os (PO, oral administration), in drinking water); anti-CTGF antibody (CLN-1, 10 mg/kg, IP injection, three times per week for 6 weeks)+Losartan 20 mg/kg/day in drinking water.

Figure 9:
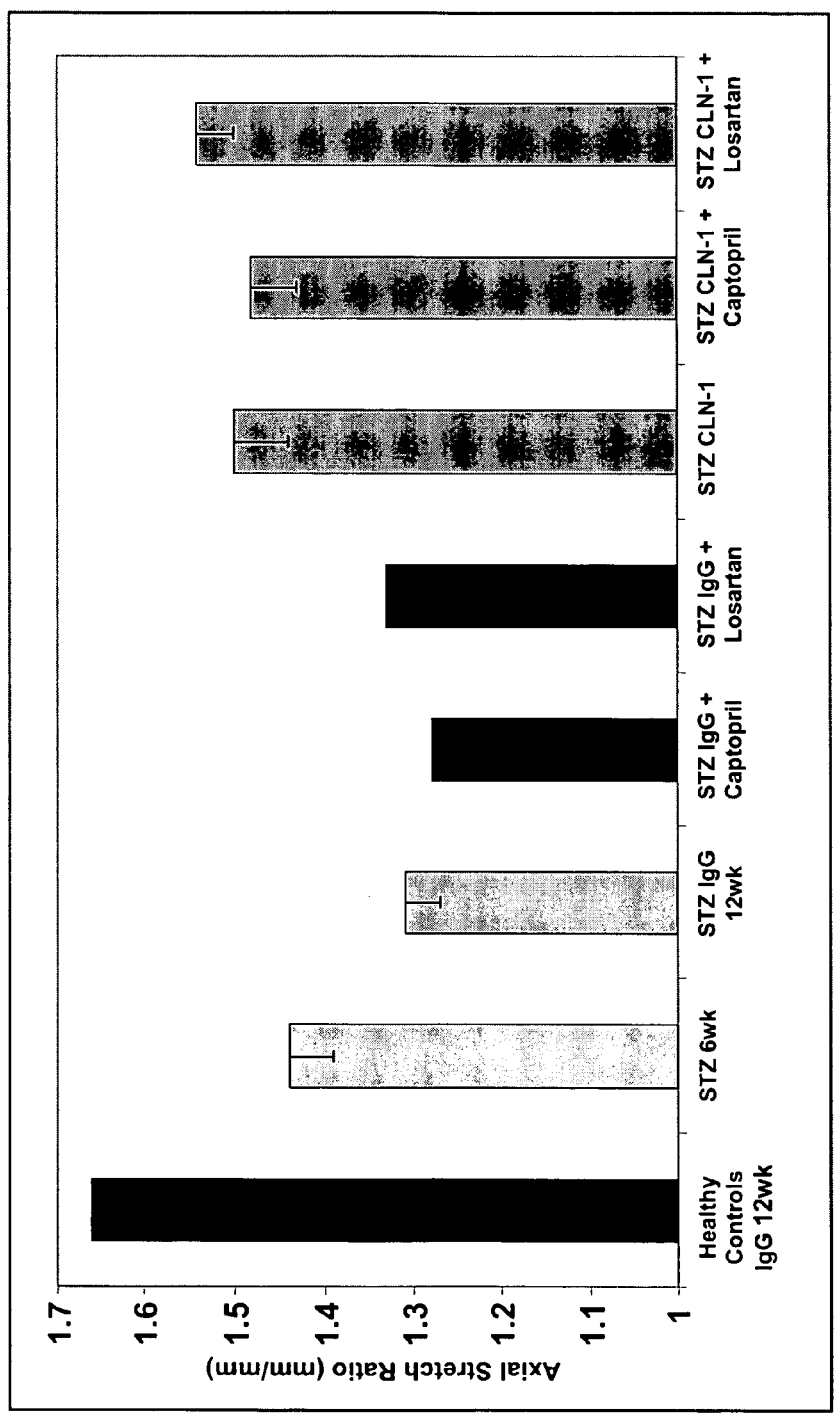
FIG. 9 shows the present methods and agents effectively reversed decreases in the in vivo axial stretch ratio in mammalian subjects.

Animals in this study underwent arterial mechanical property testing as described in Example 1. The length of the arterial segment was measured in vivo prior to mechanical property testing. To obtain data on the no-load and zero-stress state, the length of the specimen was measured 20 min after the mechanical tests. This length was compared to the in-vivo segment length measured prior to harvest of the vessel. The resulting ratio was reported as the in-vivo axial stretch ratio. Experimental diabetes decreases the in vivo axial stretch ratio by six weeks as shown in FIG. 9. Treatment with anti-CTGF antibody prevented further decreases in the in-vivo axial stretch ratio through week 12, whereas the in-vivo axial stretch ratio continued to decrease in vehicle treated animals. This decrease in in-vivo stretch ratio indicates stiffening of the artery. Arterial stiffening was prevented by treatment with anti-CTGF antibody.

Reversal of Increased Opening Angles in Large Artery Rings

Figure 10:
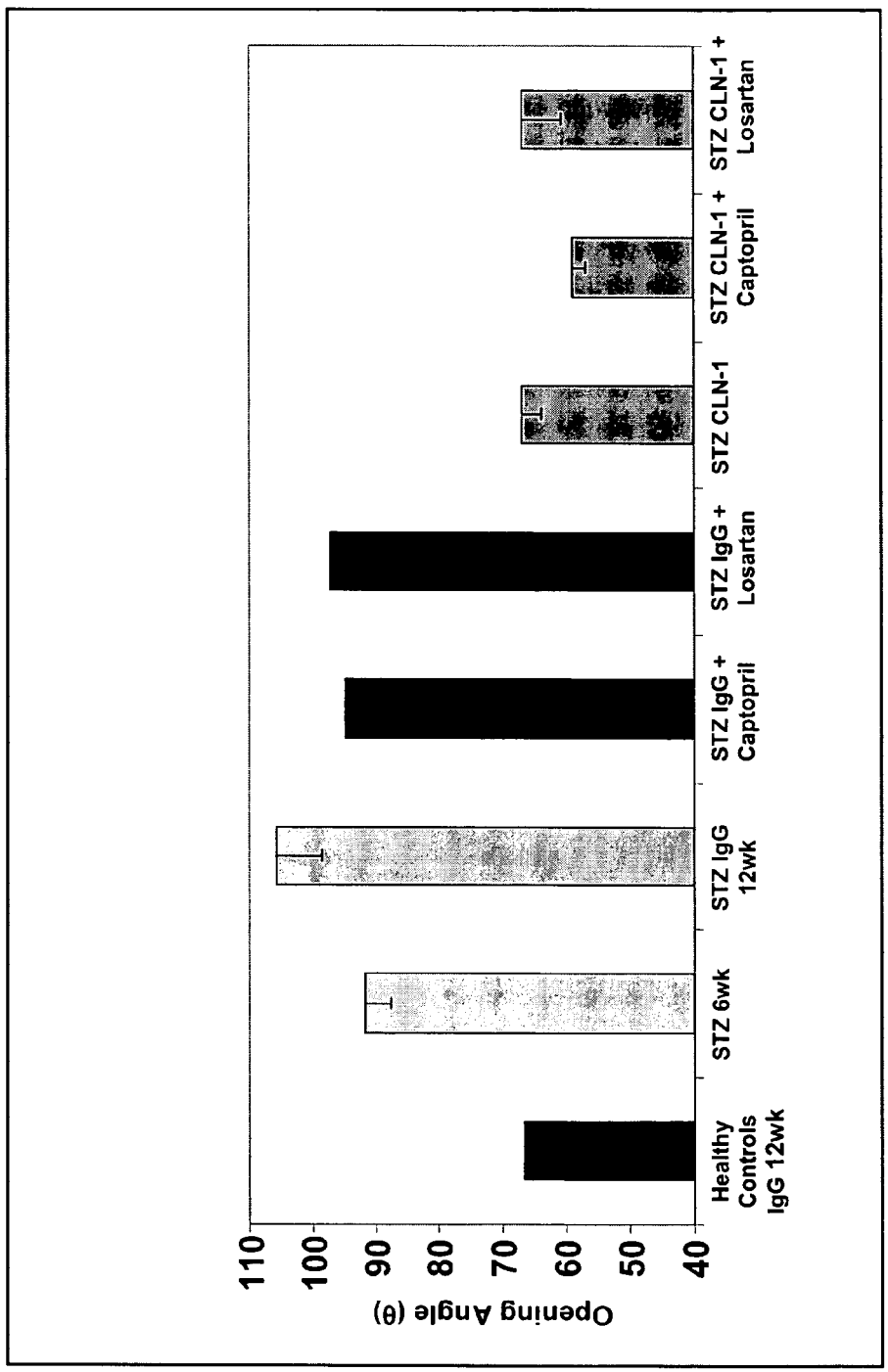
FIG. 10 shows the present methods and agents effectively reversed increases in opening angles in large artery rings in mammalian subjects.

An arterial ring was excised from the middle region of the isolated carotid segment and placed in Krebs solution. A digital photograph was taken of the cross-section of the ring in the no-load state. A radial cut was made in the ring, which opened into a sector. Digital photos were taken after 20 minutes to allow viscoelastic creep to take place. The opening angle is defined as the angle between the lines connecting the midpoint of the inner surface to the inner tips of the sector, and characterizes the zero stress state. Experimental diabetes increased the opening angle by six weeks as shown in FIG. 10. Treatment with anti-CTGF antibody normalized the increased opening angle by week 12 to levels not different from healthy controls, whereas the opening angle continued to increase in vehicle treated animals. Opening angles are an indication of residual stress in the arterial walls.

These results showed that treatment of diabetic animals with anti-CTGF antibody prevented and reversed pathologic changes in the arterial wall. (e.g., prevented and reduced vascular dysfunction, and in particular, prevented and reduced macrovascular dysfunction) of the carotid artery, and that treatment with anti-CTGF antibody was effective at reversing stiffness associated with diabetes. Taken together, these data showed that inhibition of CTGF provided a method to reduce, prevent, or reverse increases in arterial and vascular stiffness associated with diabetes (e.g., reduced or reversed vascular dysfunction, in particular, reduced or reversed macrovascular dysfunction). Therefore, inhibition of CTGF provides an effective therapeutic approach for treating vascular complications associated with diabetes and for improving vascular function. Additionally, these results indicated that methods and compounds of the present invention are effective at treating, preventing, reducing, or reversing macrovascular complications associated with diabetes and are thus useful for improving macrovascular function.

Example 3

Anti-CTGF Therapy Reduces Vascular Permeability

The effect of anti-CTGF therapy on vascular permeability (a measure of vascular function, in particular microvascular function) was measured using the animal model of diabetes described above in Example 1. At various times after the induction of diabetes, rats were tested for increased vascular permeability (VP) as follows. Unanesthetized rats were given intravenous injections of Evans Blue (EB) dye (20 mg/kg). Twenty minutes later, animals were sacrificed by anesthetic overdose and their hearts removed. Skin sections from the trunk, posterior to the shoulder, were removed and weighed. In this assay, increased vascular permeability is characterized by extravasation of dye into the skin. The skin was immersed in formamide (4 ml/g wet weight) at 24° C. for 24 hours. The absorbance of EB dye extracted in formamide was then measured by spectrophotometry at 620 nm using a plate reader. In this assay, the concentration of EB dye is proportional to the degree of vascular permeability. In addition, sections of skin were taken with a 6 mm biopsy punch. These sections were weighed and then dried overnight at 60° C. The dried samples were weighed and the wet weight to dry weight ratio was determined. An increase in the wet/dry ratio is indicative of tissue edema.

Figure 11:
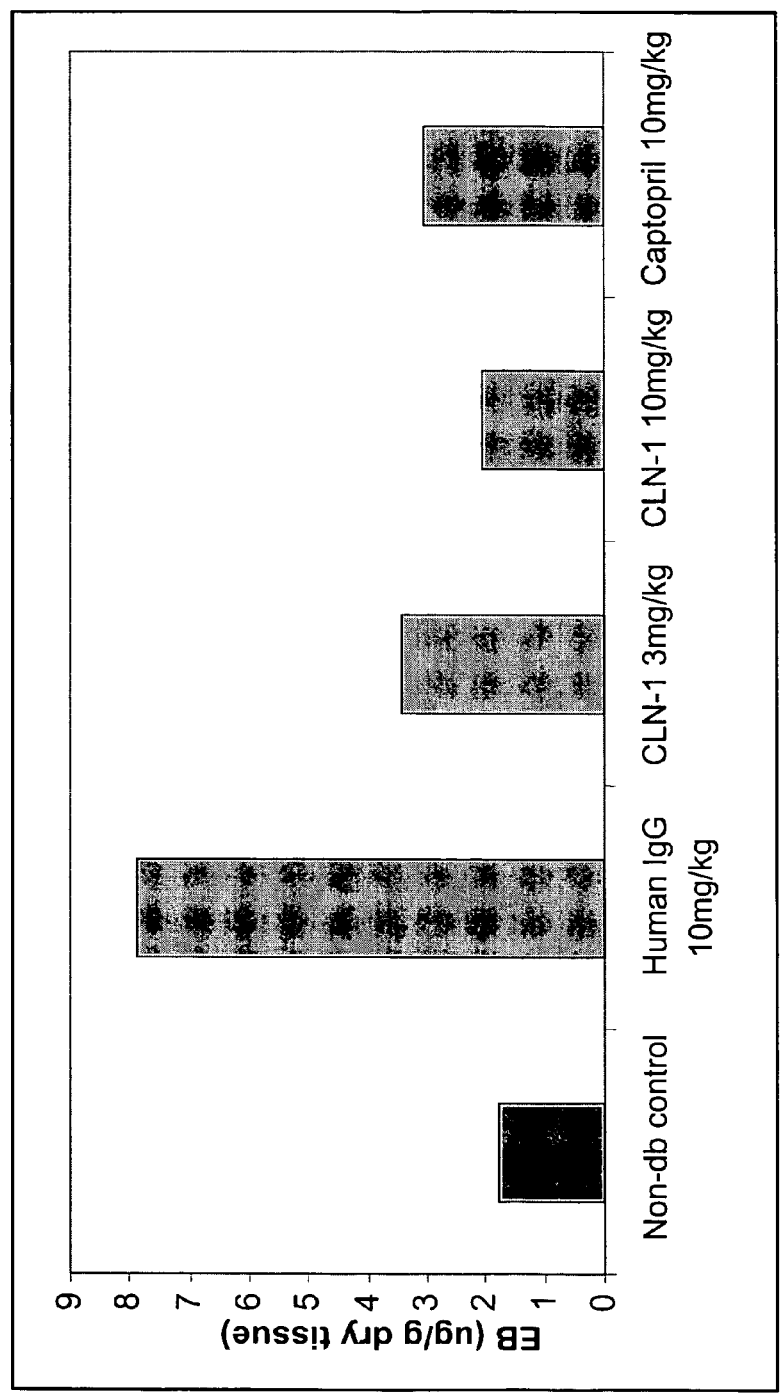
FIG. 11 shows the present methods and agents effectively reduced extravascular edema in mammalian subjects.
Figure 12:
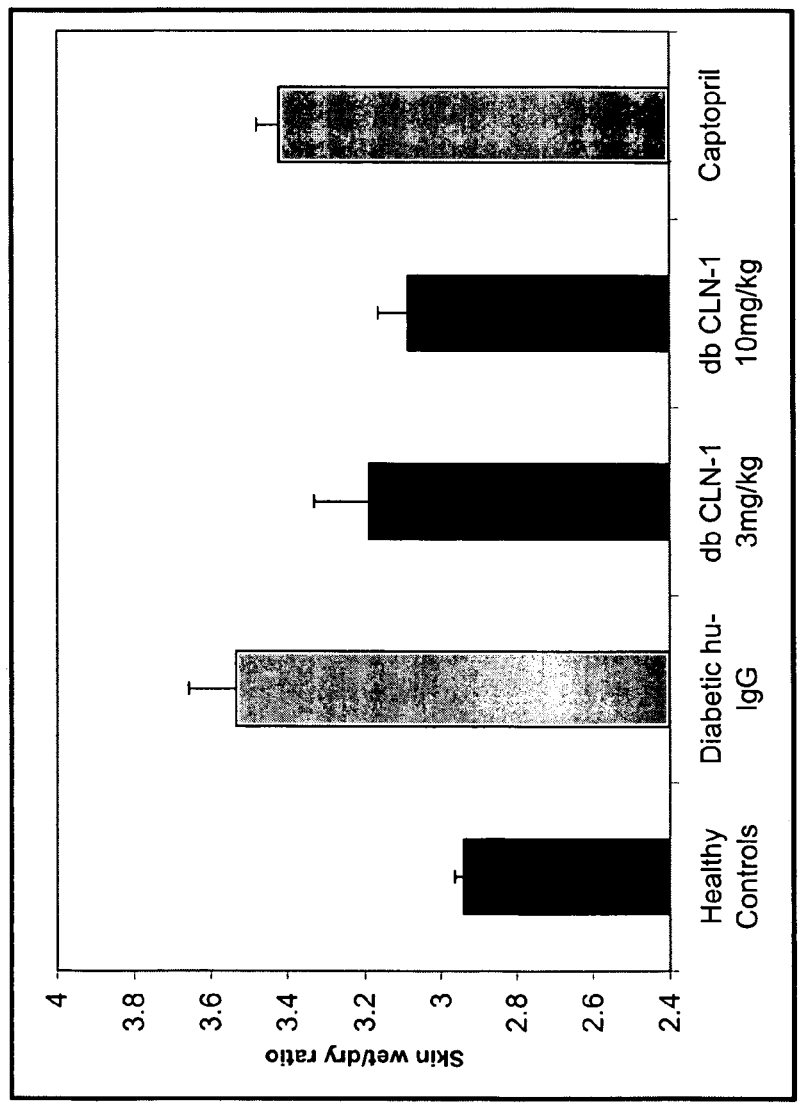
FIG. 12 shows the present methods and agents effectively reduced vascular permeability in mammalian subjects.

As shown in FIG. 11 and FIG. 12, diabetic animals at 3 weeks had increased vascular permeability and tissue edema (compared to control non-diabetic animals) as evidenced by increased Evans Blue extravasation and increased wet/dry ratios in the tissue. Diabetic animals treated with anti-CTGF antibody had reduced Evans Blue extravasation and reduced wet/dry ratio compared to non-treated diabetic animals.

These results showed that treatment of diabetic animals with anti-CTGF antibody reduced vascular permeability and reduced tissue edema associated with diabetes (e.g., reduced vascular dysfunction, in particular microvascular dysfunction). Taken together, these results indicated that methods and compounds of the present invention are effective at treating, preventing, or reducing microvascular complications associated with diabetes and are thus useful for improving microvascular function.

Figure 13:
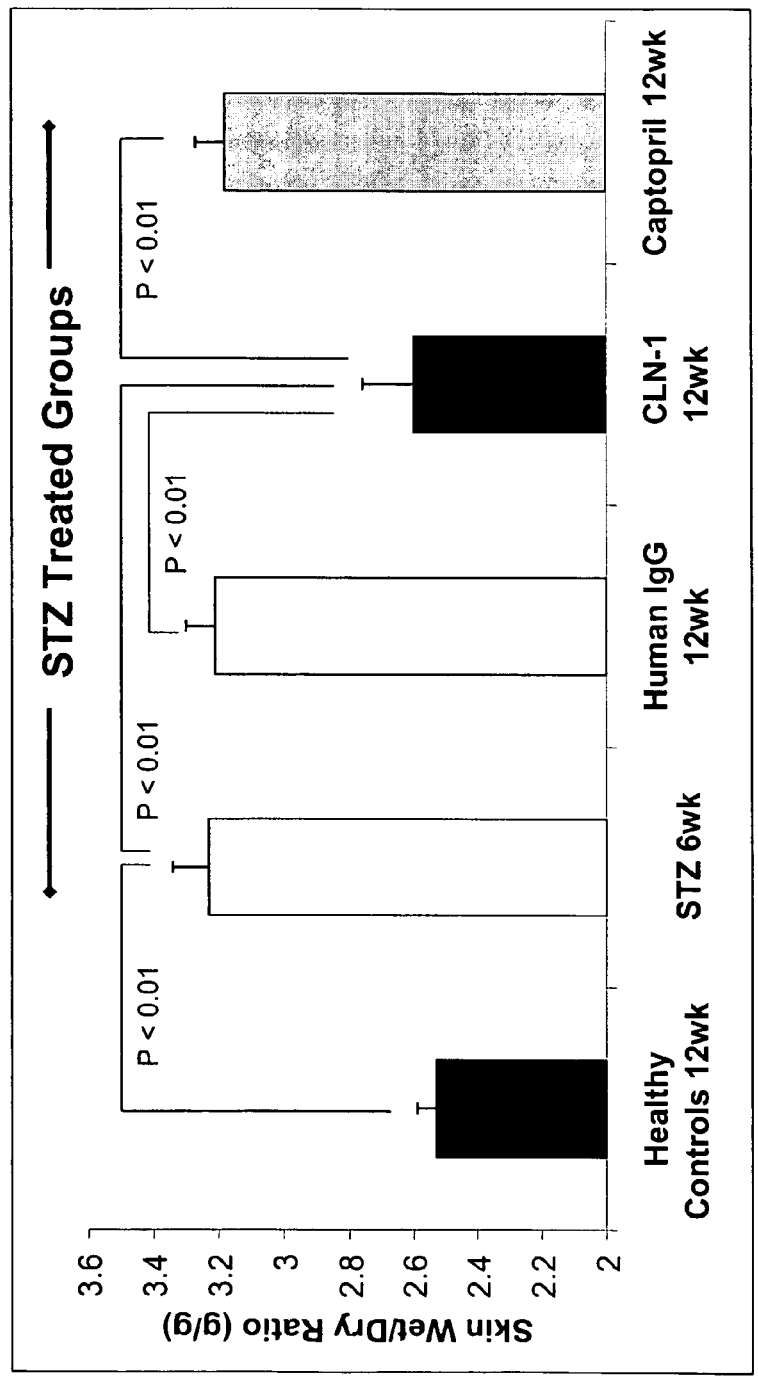
FIG. 13 shows the present methods and agents effectively reduced and reversed vascular permeability and extravascular edema associated with diabetes in mammalian subjects.

As shown in FIG. 13, diabetic animals at 6 weeks, and diabetic animals administered control HuIgG from week 6 to week 12 following STZ injection and development of diabetes, had increased vascular permeability and tissue edema (compared to control non-diabetic animals) as evidenced by increased Evans Blue extravasation and increased wet/dry ratios in the tissue. (Data shown in FIG. 13 analyzed by ANOVA followed by LSD post hoc tests.) Diabetic animals treated with anti-CTGF antibody (from week 6 through week 12) showed reduced Evans Blue extravasation and reduced wet/dry ratio compared to non-treated diabetic animals. Additionally, animals administered anti-CTGF antibody from week 6 through week 12 showed reduced vascular permeability and tissue edema compared to that observed in control animals administered control human IgG. These results indicated that anti-CTGF antibody treatment was effective at improving, reducing, and reversing vascular permeability and tissue edema associated with diabetes.

These results showed that treatment of diabetic animals with anti-CTGF antibody reduced and reversed vascular permeability and reduced and reversed tissue edema associated with diabetes (e.g., reduced and reversed vascular dysfunction, in particular, reduced and reversed microvascular dysfunction). Taken together, these results indicated that methods and compounds of the present invention are effective at treating, preventing, reducing, or reversing microvascular complications associated with diabetes and are thus useful for improving microvascular function.

Example 4

Anti-CTGF Therapy Reduces Vascular Calcification

The effect of anti-CTGF therapy on vascular calcification was examined as follows. Von Kossa stain for calcium mineral deposits was performed on carotid artery sections obtained from animals six weeks after the induction of diabetes with STZ. Two-centimeter segments of common carotid artery were placed in 10% zinc formalin (0.1 M) for 24 hours, dehydrated in a graded series of ethanol solutions, and then embedded in paraffin. Three-micrometer thick sections of the carotid tissue were cut, deparaffinized, hydrated in distilled water, and then treated with 5% $AgNO_3$ for sixty minutes. Carotid artery tissue specimens were then rinsed in distilled water and treated with 5% $Na_2S_2O_3$ for two minutes. The specimens were then sequentially rinsed in distilled water and 95% ethanol. The specimens were then counterstained with eosin, examined under light microscope, and scored for vascular wall calcification by the presence of dark black/brown staining along the intima layer of the vessel wall. Vascular calcification was measured as being present or not present in the vascular wall observed under a light microscope.

Figure 14:
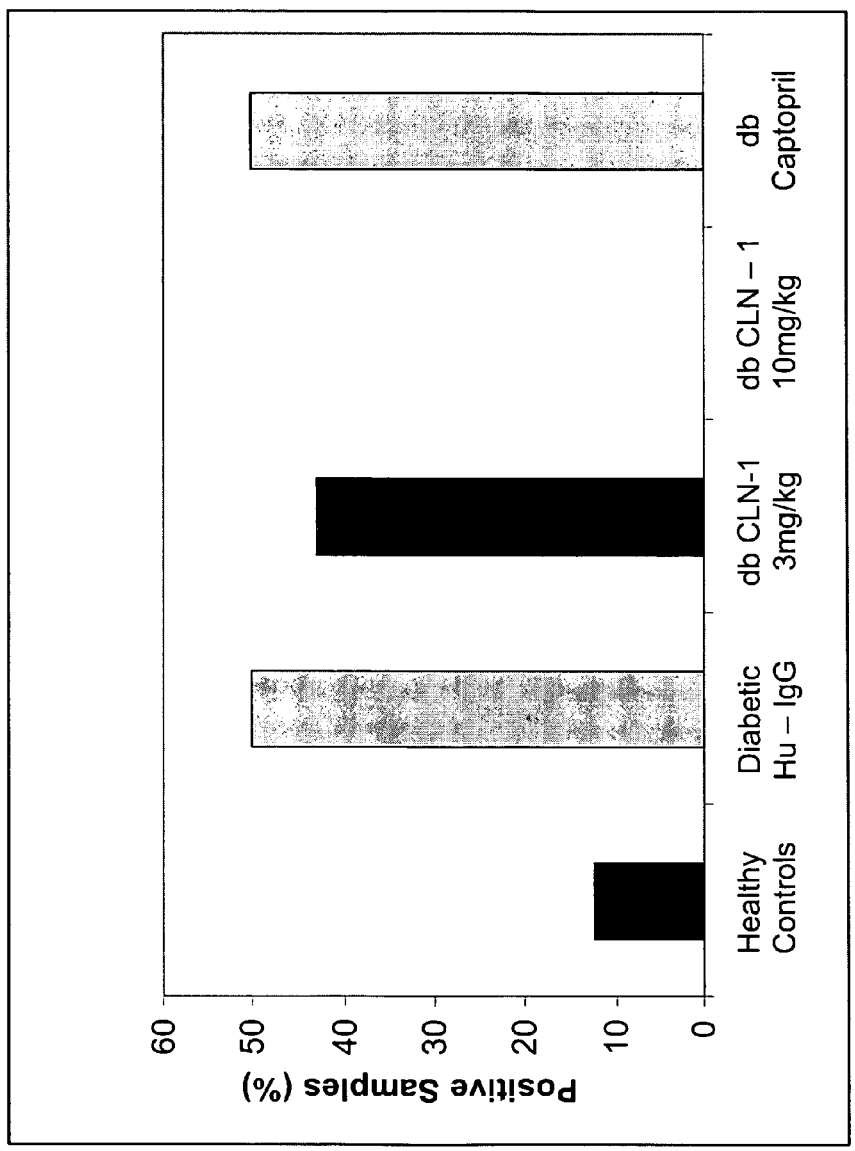
FIG. 14 shows the present methods and agents effectively reduced vascular calcification in mammalian subjects.

The results of this study are shown in FIG. 14. Six weeks after the induction of diabetes, von Kossa staining for calcium mineral deposits associated with the vasculature showed strong positive black/brown-staining areas along the intima layer of carotid arteries obtained from diabetic animals; whereas carotid arteries obtained from non-diabetic animals showed little or no calcium staining. Additionally, half of the carotid arteries obtained from diabetic animals treated with control human-IgG (n=6) showed strong positive staining for vascular calcification. Similarly, half of the carotid arteries obtained from diabetic animals treated with Captopril demonstrated strong calcium staining at six weeks (n=8). Carotid arteries obtained from diabetic animals administered anti-CTGF antibody (CLN-1, 3 mg/kg) showed reduced staining for calcium mineral deposits. Specifically, less than half (43%) of the carotid arteries from diabetic animals treated with 3 mg/kg of anti-CTGF antibody (CLN-1) showed positive calcium staining at six weeks. Administration of a higher does of anti-CTGF antibody (CLN-1, 10 mg/kg) prevented calcium deposition in all of the carotid sections obtained from diabetic animals (n=6). These results showed that treatment of diabetic animals with anti-CTGF antibody prevented or reduced vascular calcification. This data indicated that anti-CTGF therapy would be useful for preventing or reducing vascular calcification.

Example 5

Anti-CTGF Therapy has Therapeutic Benefit in Diabetic Animal Models of Cardiovascular Complications Eight-week-old male db/db mice (C57BLKS/J-leprdb/leprdb) and their age-matched non-diabetic db/+littermates (C57BLKS/J-leprdb/+) (Jackson Labs, Bar Harbor, Me.) were used. db/db mice had an initial weight of ~40 g. Non-diabetic db/+mice had an initial body weight of ~20 g. In certain experimental groups, drinking water included the addition of Losartan (200 mg/L), a concentration to ensure a delivery of ~2 mg/day of Losartan.

Purified, multi-donor human IgG was purchased from Sigma Chemical Corporation (St. Louis, Mo.) and re-purified by Protein A chromatography. Acid eluate containing human IgG was immediately neutralized and dialyzed exhaustively against PBS and then sterile-filtered, tested to verify purity and absence of endotoxin, and stored at 4° C. until use (Batch No. CML 052803 or similar, 4.67 mg/mL).

Anti-CTGF monoclonal antibody (CLN-1) treatment was initiated at 8 weeks of age once 100% of the db/db mice become frankly hyperglycemic as evidenced by levels of blood glucose elevated two-fold or more above the db/+control mice. Following the development of diabetes as determined by hyperglycemia, the db/db mice were randomized into groups of 10 mice per group and treated as follows. One group of db/db mice was treated with i.p. injections of anti-CTGF antibody (3 mg/kg), another group was treated with anti-CTGF antibody (CLN-1, 10 mg/kg); another group was treated with an isotype-matched irrelevant human IgG (cIgG, 10 mg/kg)); another group received Losartan (2 mg/day) in their drinking water; and another group received both Losartan in their drinking water (2 mg/day) and were injected IP with cIgG (10 mg/kg). Antibodies were administered IP in an initial bolus dose of 300 micrograms, followed by doses of 3 mg/kg or 10 mg/kg (approximate injection volume of 0.5 ml) three times weekly for 8 weeks.

At animal sacrifice, non-fasting blood samples were drawn from the retro-orbital venous plexus using heparinized capillary tubes. Unseparated heparinized blood was analyzed for HbA1c and lipid levels. Serum samples were stored at −80° C. until analysis was performed. The right and left kidneys, the liver, and the heart were removed from each animal and weighed.

Blood lipid determination was performed as follows: Levels of total cholesterol (TC), HDL, and triglycerides (TG) were measured by a commercially available test kit (PTS Panels, Polymer Technology Systems, Inc.). Levels of LDL were calculated by the following formula: LDL=TC−HDL−(TG/5). Levels of glycated hemoglobin (measured as % glycated hemoglobin, HbA1c) were determined on fresh whole blood by a validated commercially available HbA1c test kit.

Figure 15:
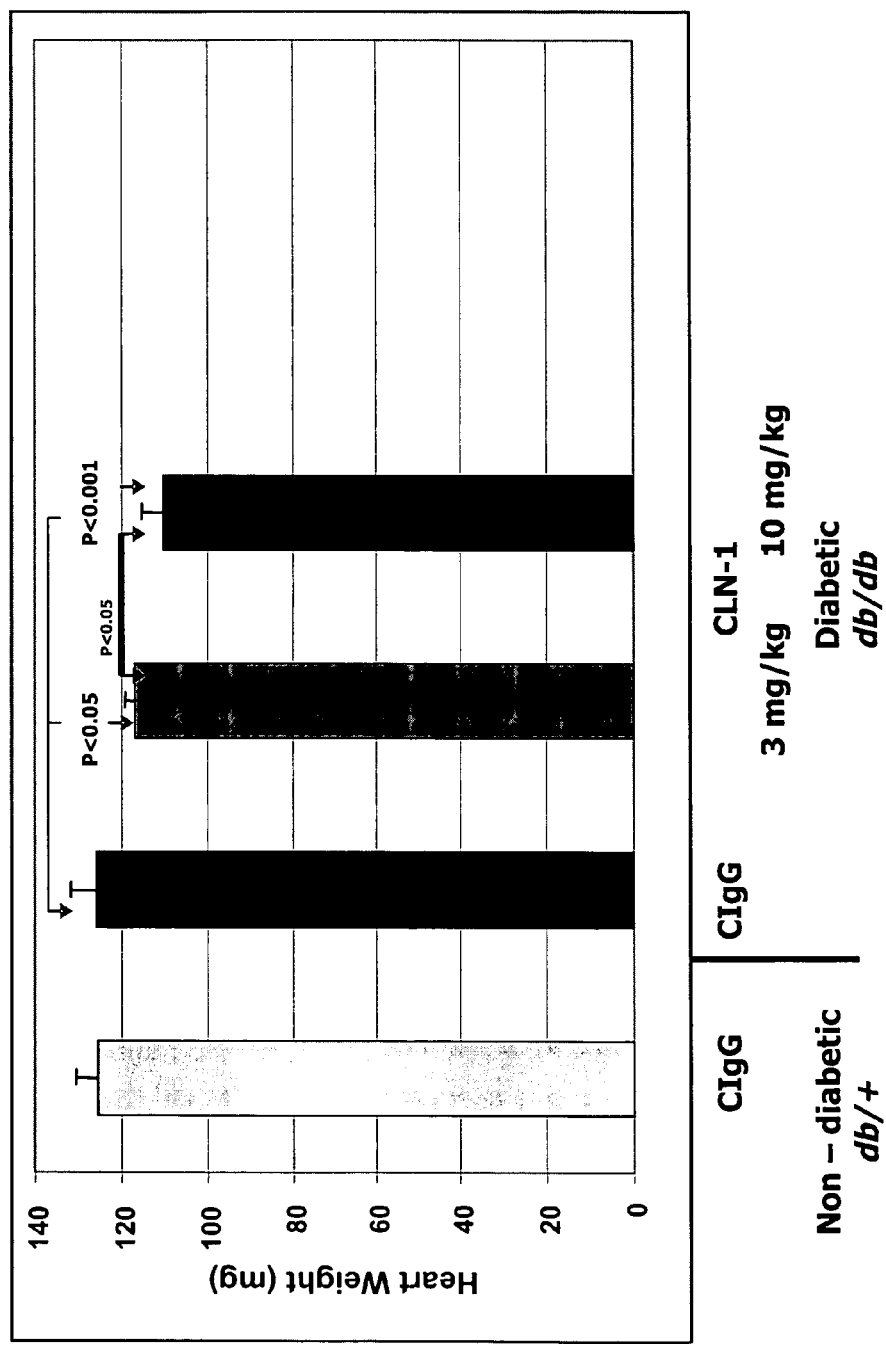
FIG. 15 shows the present methods and agents effectively reduced heart weight in an animal model of diabetes.
Figure 16:
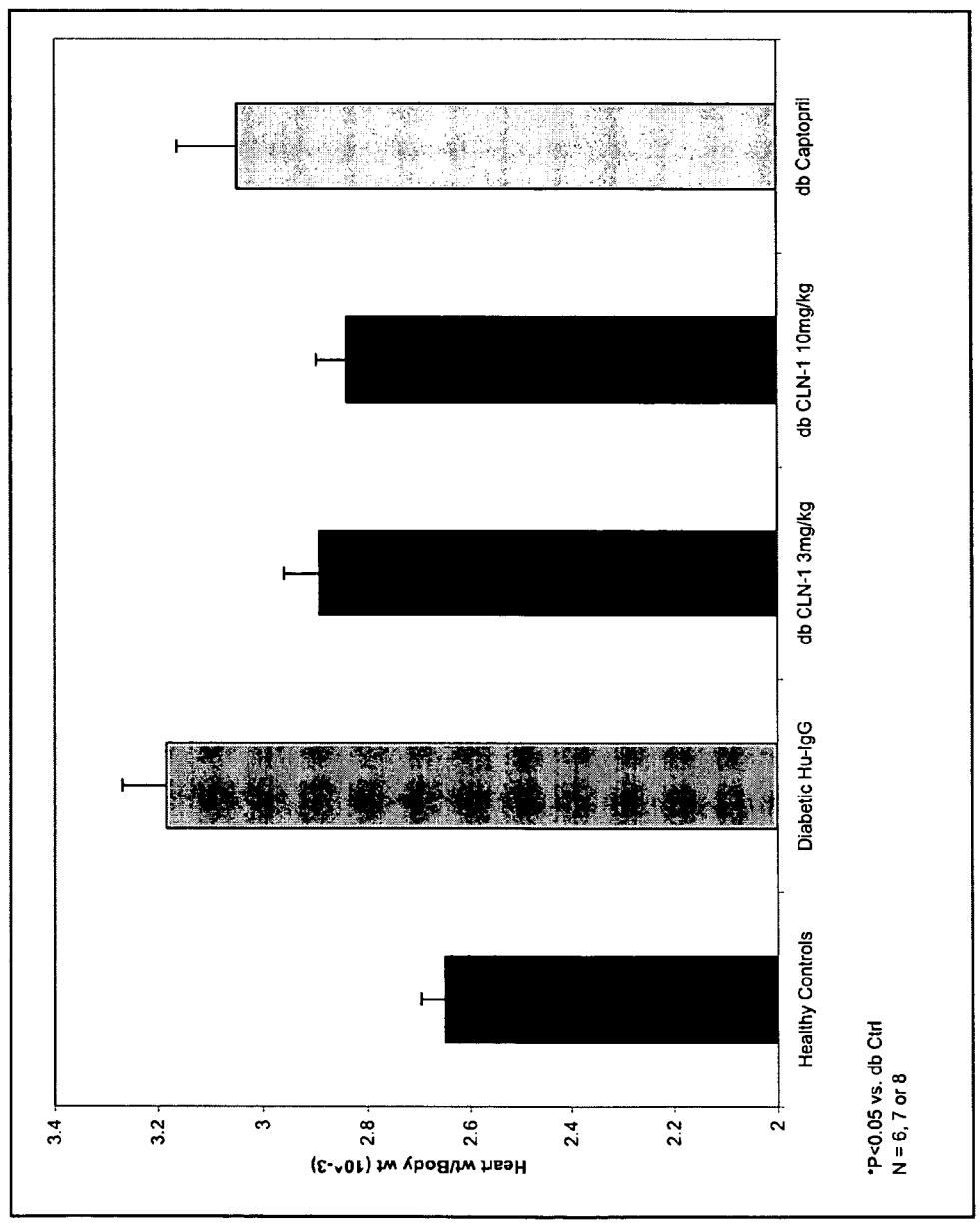
FIG. 16 shows the present methods and agents effectively reduced heart weight to body weight ratio in mammalian subjects.

As shown in FIG. 15, diabetic animals administered anti-CTGF antibody had reduced heart weights compared to that of diabetic animals administered control IgG. These results suggested that anti-CTGF therapy is useful for treating cardiovascular disorders associated with diabetes, including cardiac hypertrophy, congestive heart failure, and cardiomyopathy. FIG. 16 shows anti-CTGF antibody administration reduced the heart weight to body weight ratio in the STZ-induced diabetic rat model, as described above in Example 1.

Figure 17:
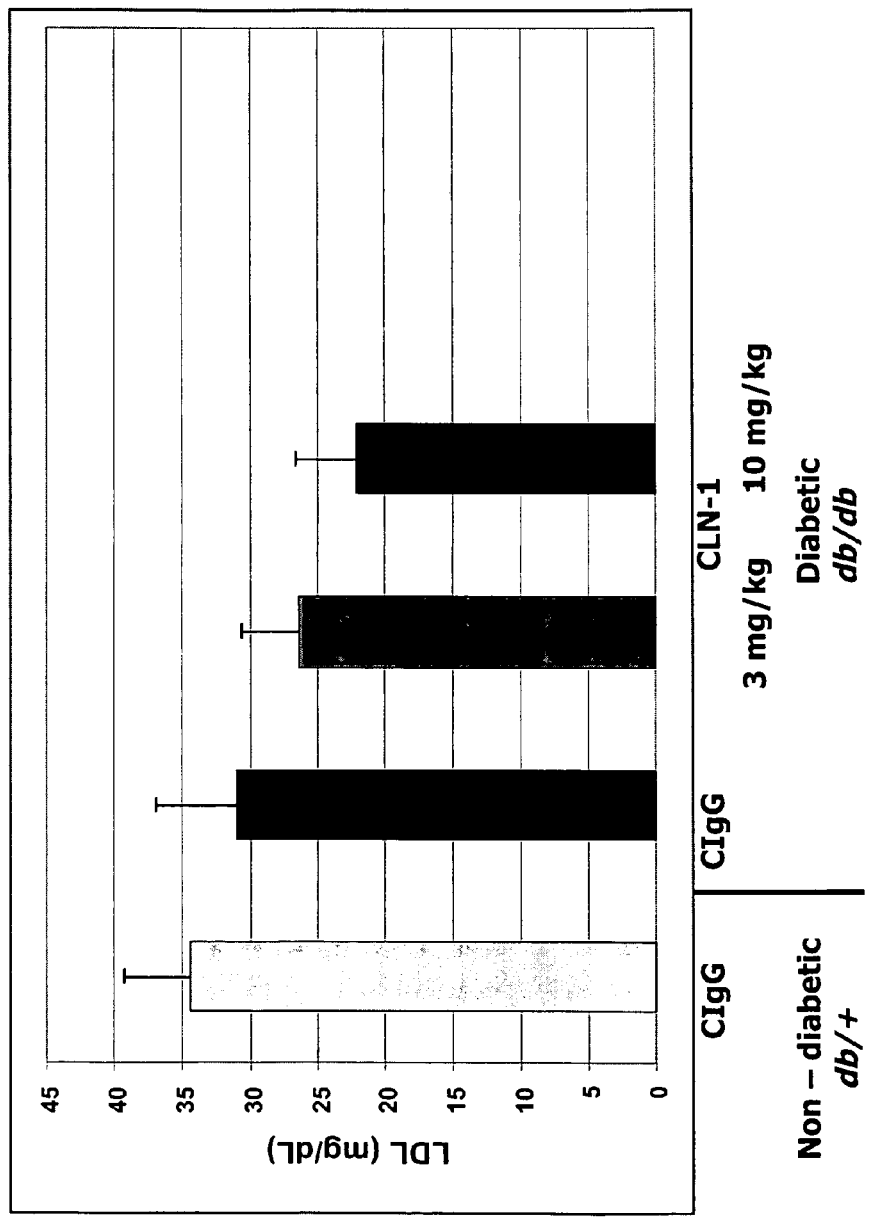
FIG. 17 shows the present methods and agents effectively reduced blood low-density lipoprotein (LDL) levels in mammalian subjects.

As shown in FIG. 17, administration of anti-CTGF antibody to diabetic animals reduced blood LDL levels. Increased LDL levels are a risk factor for development of cardiovascular diseases and disorders. Therefore, these results suggested that anti-CTGF therapy is useful for reducing the risk of developing or preventing development of cardiovascular disease by reducing LDL levels.

Figure 18:
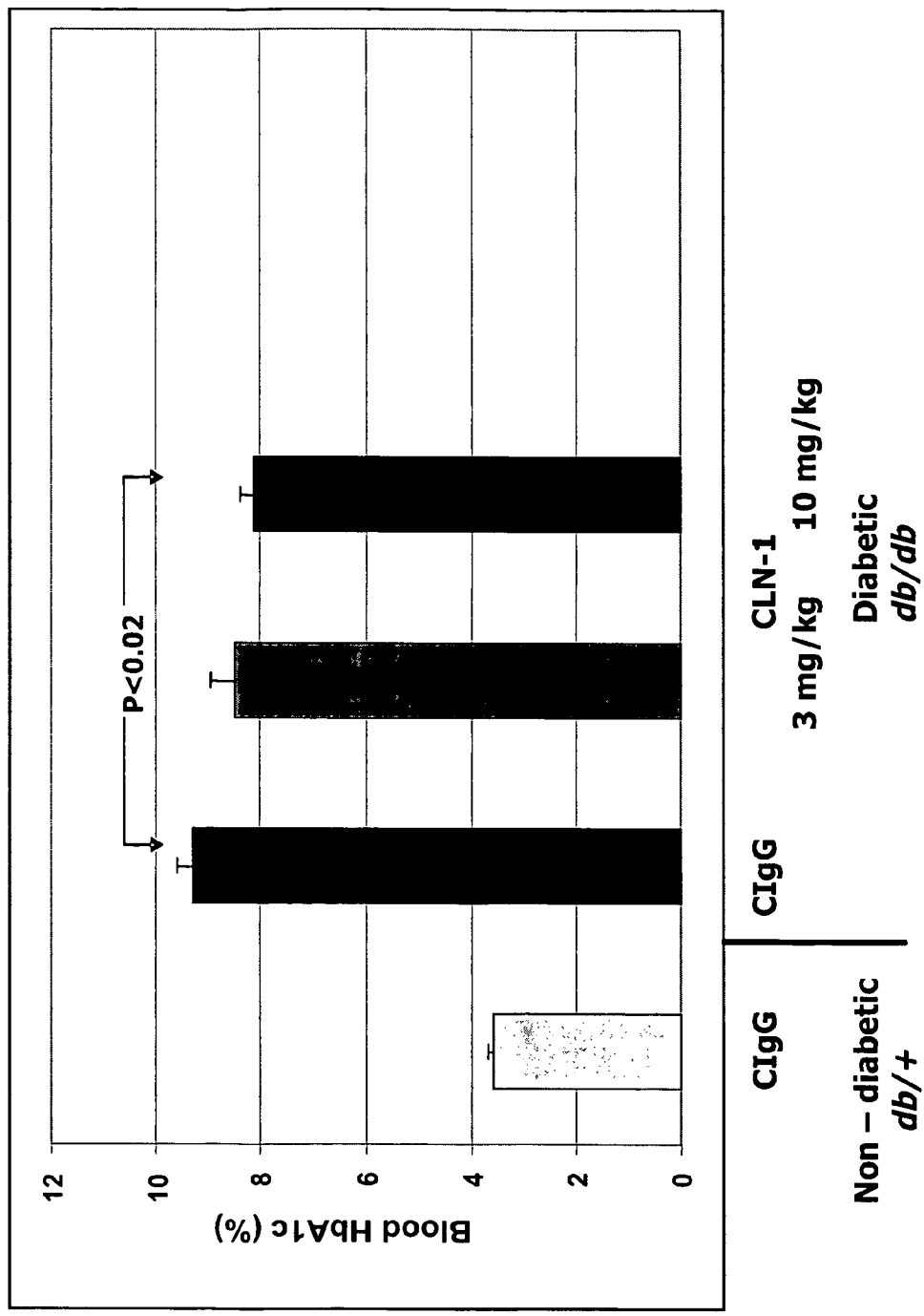
FIG. 18 shows the present methods and agents effectively reduced blood HbA1c levels in mammalian subjects.
Figure 19:
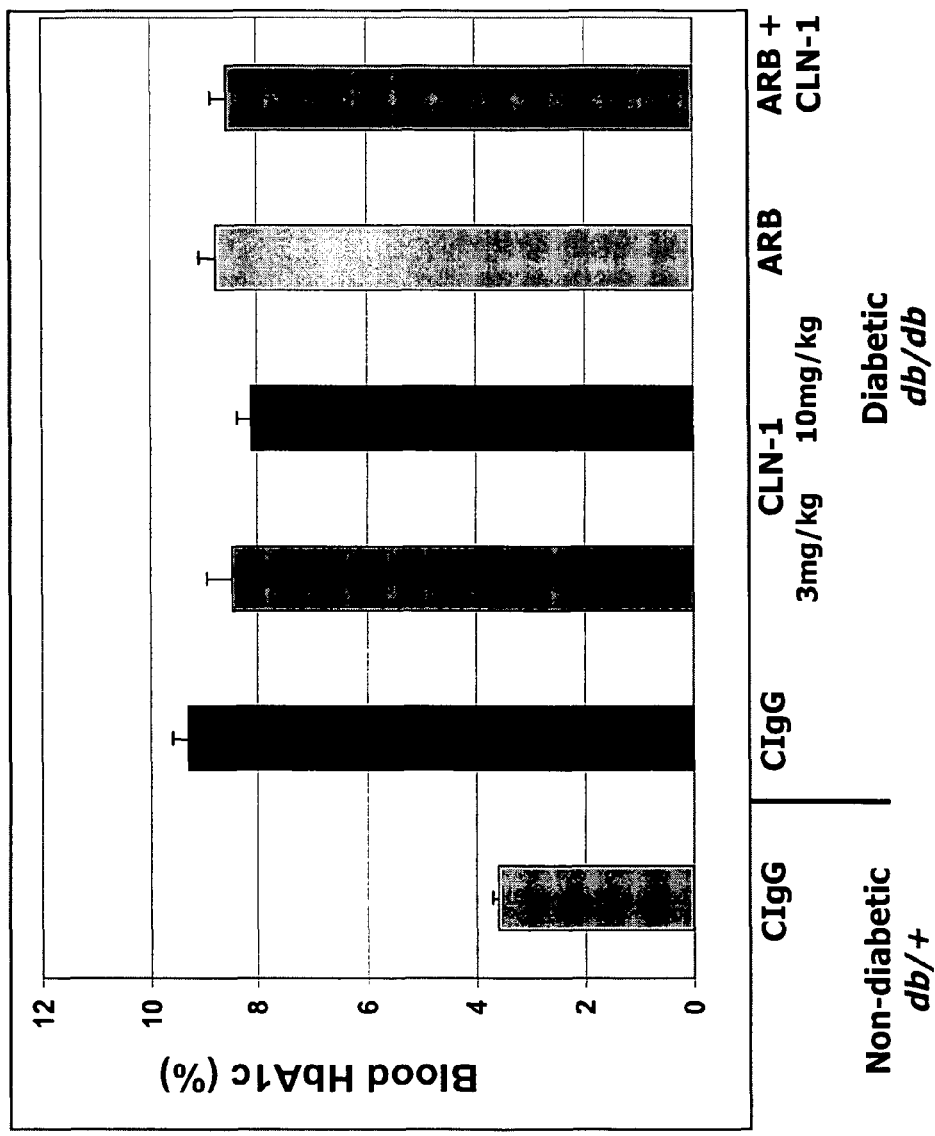
FIG. 19 shows the present methods and agents effectively reduced blood HbA1c levels in mammalian subjects.

FIG. 18 shows that administration of anti-CTGF antibody to diabetic animals reduced blood HbA1c (glycated hemoglobin) levels. FIG. 19 shows anti-CTGF antibody administration reduced blood HbA1c levels in the STZ-induced diabetic rat model, as described above in Example 1. Measurement of glycated hemoglobin levels provides an accurate index of the mean blood glucose concentration over the preceding 2 to 3 months in humans. In humans, normal (non-diabetic) glycated hemoglobin levels are in the range of 4 to 6%. In the study of diabetic human individuals, the DCCT found that lowering or maintaining HbA1c levels to an average HbA1c level of 7.2% resulted in a 35% reduction in cardiovascular disease compared to diabetic individuals with higher HbA1c levels. Therefore, these results suggested that anti-CTGF therapy is useful for reducing glycated hemoglobin levels, thereby reducing the risk of developing or preventing development of cardiovascular disease.

Figure 20:
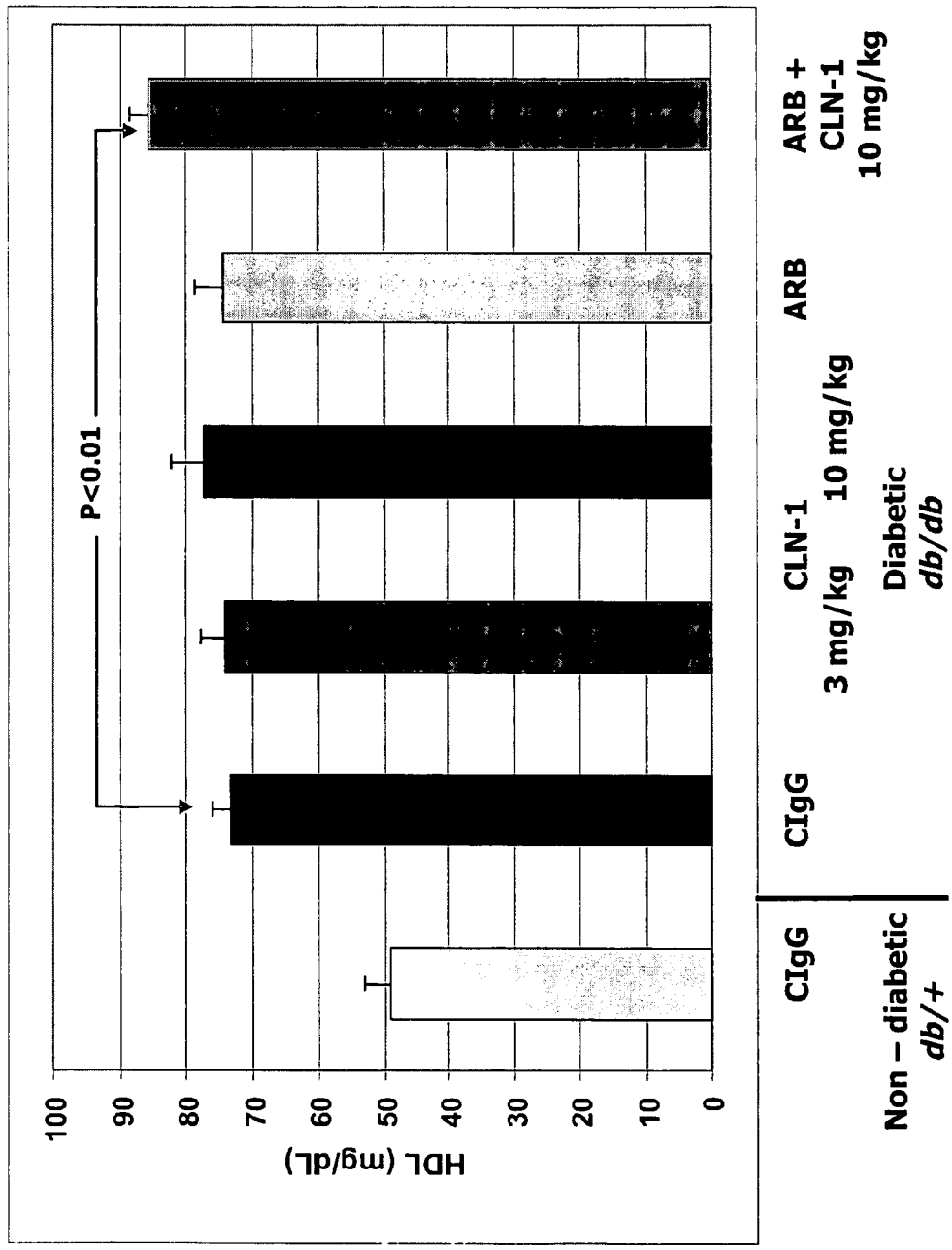
FIG. 20 shows anti-CTGF antibody administration in combination with angiotensin receptor blocker (ARB) therapy increased blood HDL levels in mammalian subjects.

FIG. 20 shows that combination therapy of anti-CTGF antibody and ARB are effective at increasing blood HDL levels.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

Each of the following references is incorporated by reference herein in its entirety.

REFERENCES

1. Roestenberg, P. et al. Connective tissue growth factor is increased in plasma of type 1 diabetic patients with nephropathy. *Diabetes Care* 27:1164-1170 (2004).
2. Jaffa, A. A. et al. Connective Tissue Growth Factor (CTGF) N Fragment: a marker of progressive diabetic nephropathy. *Amer. Soc. Neprol.* (2002 Annual Meeting).
3. Gilbert, R. E. et al. Urinary connective tissue growth factor excretion in patients with type 1 diabetes and nephropathy. *Diabetes Care* 26:2632-36 (2003).
4. Lemley, K. V. et al. Urinary excretion of connective tissue growth factor increases with disease severity in IgA nephropathy and type 2 diabetic nephropathy. *J. Am. Soc. Nephrol.* (2001 Annual Meeting).
5. Ito, Y. et al. Human urinary CTGF (CCN2) as a predictor of progression of chronic renal disease. *Amer. Soc. Nephrol.* (2003 Annual Meeting).
6. Murphy, M. et al. Suppression subtractive hybridization identifies high glucose levels as a stimulus for expression of connective tissue growth factor and other genes in human mesangial cells. *J. Biol. Chem.* 274(9):5830-4 (1999).
7. Lam, S. et al. Connective tissue growth factor and igf-I are produced by human renal fibroblasts and cooperate in the induction of collagen production by high glucose. *Diabetes* 52:2975-2983 (2003).

8. Hishikawa, K. et al. Static pressure regulates connective tissue growth factor expression in human mesangial cells. *J. Biol. Chem.* 276(20): 16797-16803 (2001).
9. Twigg, S. M. et al. Advanced glycosylation end products up-regulate connective tissue growth factor (insulin-like growth factor-binding protein-related protein 2) in human fibroblasts: a potential mechanism for expansion of extracellular matrix in diabetes mellitus. *Endocrinology* 142(5):1760-9 (2001).
10. Suzuma, K. et al. Vascular endothelial growth factor induces expression of connective tissue growth factor via KDR, Flt1, and phosphatidylinositol 3-kinase-akt-dependent pathways in retinal vascular cells. *J. Biol. Chem.* 275(52):40725-31 (2000).
11. Ruiz-Ortega, R. M. et al. Angiotensin II increases connective tissue growth factor in the kidney. *Am. J. Pathol.* 163(5):1937-47 (2003).
12. Abdel-Wahab, N. et al. Connective tissue growth factor and regulation of the mesangial cell cycle: role in cellular hypertrophy. *J. Am. Soc. Nephrol.* 13:2437-2445 (2002).
13. Riser, B. L. et al. Regulation of connective tissue growth factor activity in cultured rat mesangial cells and its expression in experimental diabetic glomerulosclerosis. *J. Am. Soc. Nephrol.* 11:25-38 (2000).
14. Liu, B. C. et al. Role of connective tissue growth factor in mediating hypertrophy of human proximal tubular cells induced by angiotensin II. *Am. J. Nephrol.* 23(6): 429-437 (2003).
15. Igarashi, A. et al. Regulation of connective tissue growth factor gene expression in and during wound repair. *Mol. Biol. Cell.* 4(6):637-645 (1993).
16. Gilbert, R. E. et al. Expression of transforming growth factor-beta1 and type IV collagen in the renal tubulointerstitium in experimental diabetes: effects of ACE inhibition. *Diabetes.* 47(3):414-22 (1998).
17. He, S. et al. A role for connective tissue growth factor in the pathogenesis of choroidal neovascularization. *Arch. Ophthalmol.* 121:1283-1288 (2003).
18. Kuiper, E. J. et al. Connective tissue growth factor in vitreous correlates with fibrosis in vitreoretinal disorders in the human eye. The Association for Research in Vision and Ophthalmology. 4145 (2004 Annual Meeting)
19. Oemar, B. S. and Luscher, T. F. Connective tissue growth factor. Friend or foe? *Arterioscler. Thromb. Vasc. Biol.* 17(8):1483-9 (1997).
20. Finckenberg, P. et al. Angiotensin II induces connective tissue growth factor gene expression via calcineurin-dependent pathways. *Am. J. Pathol.* 163(1):355-366 (2003).
21. Liu, B. C. et al. Mechanisms of irbesartan in prevention of renal lesion in streptozotocin-induced diabetic rats. *Acta. Pharmacol. Sin.* 24(1):67-73 (2003).
22. Ahmed, M. S. et al. Connective tissue growth factor—a novel mediator of angiotensin II-stimulated cardiac fibroblast activation in heart failure in rats. *J. Mol. Cell. Cardiol.* 36(3):393-404 (2004).
23. Peng, H. et al. Ac-SDKP reverses cardiac fibrosis in rats with renovascular hypertension. *Hypertension.* 42(6): 1164-70 (2003).
24. Kapoun, A. M. et al. B-type natriuretic peptide exerts broad functional opposition to transforming growth factor-beta in primary human cardiac fibroblasts: fibrosis, myofibroblast conversion, proliferation, and inflammation. *Circ. Res.* 5; 94(4):453-61 (2004).
25. Candido, R. et al. A breaker of advanced glycation end products attenuates diabetes-induced myocardial structural changes. *Circ. Res.* 92(7):785-92 (2003).
26. Goppelt-Struebe, M. et al. Regulation of connective tissue growth factor (ccn2; ctgf) gene expression in human mesangial cells: modulation by HMG CoA reductase inhibitors (statins). *Mol. Pathol.* 54(3):176-179 (2001).

What is claimed is:

1. A method for the treatment of diabetes and/or hypertension comprising administering to a subject in need thereof an effective amount of an anti-CTGF antibody in order to achieve an effect selected from the group consisting of
   a) increasing cardiac ejection fraction,
   b) increasing cardiac stroke volume,
   c) increasing cardiac output,
   d) increasing ventricular relaxation,
   e) reducing end diastolic pressure, or
   f) reducing end diastolic volume;
wherein the ejection fraction, stroke volume, cardiac output, ventricular relaxation, end diastolic pressure, or end diastolic volume is measured prior to treatment and after treatment, and the treatment is repeated until the selected effect is achieved.

2. The method of claim 1, wherein the subject is a subject having diabetes.

3. The method of claim 1, wherein the subject is a human subject.

4. A method for increasing cardiac ejection fraction in a mammalian subject in need thereof, comprising measuring cardiac ejection fraction in the subject, administering to the subject an effective amount of an anti-CTGF antibody and measuring ejection fraction after administration, wherein the cardiac ejection fraction is increased.

5. A method for increasing cardiac stroke volume in a mammalian subject in need thereof, comprising measuring cardiac stroke volume in the subject, administering to the subject an effective amount of an anti-CTGF antibody and measuring cardiac stroke volume after administration, wherein the cardiac stroke volume is increased.

6. A method for increasing cardiac output in a mammalian subject in need thereof, comprising measuring cardiac output in the subject, administering to the subject an effective amount of an anti-CTGF antibody and measuring cardiac output after administration, wherein the cardiac output is increased.

7. A method for increasing ventricular relaxation in a mammalian subject in need thereof, comprising measuring ventricular relaxation in the subject, administering to the subject an effective amount of an anti-CTGF antibody and measuring ventricular relaxation after administration, wherein the ventricular relaxation is increased.

8. A method for reducing end diastolic pressure in a mammalian subject in need thereof, comprising measuring end diastolic pressure in the subject, administering to the subject an effective amount of an anti-CTGF antibody and measuring end diastolic pressure after administration, wherein the end diastolic pressure is reduced.

9. A method for reducing end diastolic volume in a mammalian subject in need thereof, comprising measuring end diastolic volume in the subject, administering to the subject an effective amount of an anti-CTGF antibody and measuring end diastolic volume after administration, wherein the end diastolic volume is reduced.

* * * * *